US010328382B2

(12) United States Patent
Barnes et al.

(10) Patent No.: US 10,328,382 B2
(45) Date of Patent: Jun. 25, 2019

(54) APPARATUS AND SYSTEM FOR TESTING SWING ADSORPTION PROCESSES

(71) Applicants: William Barnes, Spring, TX (US); Ananda K. Nagavarapu, Houston, TX (US)

(72) Inventors: William Barnes, Spring, TX (US); Ananda K. Nagavarapu, Houston, TX (US)

(73) Assignee: ExxonMobil Upstream Research Company, Spring, TX (US)

(*) Notice: Subject to any disclaimer, the term of this patent is extended or adjusted under 35 U.S.C. 154(b) by 162 days.

(21) Appl. No.: 15/683,101

(22) Filed: Aug. 22, 2017

(65) Prior Publication Data
US 2018/0085705 A1 Mar. 29, 2018

Related U.S. Application Data

(60) Provisional application No. 62/401,435, filed on Sep. 29, 2016.

(51) Int. Cl.
*B01D 53/04* (2006.01)
*B01D 53/047* (2006.01)
*G01N 33/00* (2006.01)

(52) U.S. Cl.
CPC ..... *B01D 53/0473* (2013.01); *B01D 53/0462* (2013.01); *B01D 53/0476* (2013.01);
(Continued)

(58) Field of Classification Search
CPC .. B01D 53/04; B01D 53/0462; B01D 53/047; B01D 53/0473; B01D 53/0476;
(Continued)

(56) References Cited

U.S. PATENT DOCUMENTS 1,868,138 A 7/1932 Fisk
3,103,425 A 9/1963 Meyer
(Continued)

FOREIGN PATENT DOCUMENTS

CA 2297590 9/2000
CA 2237103 12/2001
(Continued)

OTHER PUBLICATIONS

U.S. Appl. No. 15/351,693, filed Nov. 15, 2016, Ravikovitch et al.
(Continued)

*Primary Examiner* — Frank M Lawrence, Jr.
(74) *Attorney, Agent, or Firm* — ExxonMobil Upstream Research Company—Law Department

(57) ABSTRACT

Provided are apparatus and systems for testing the performance a swing adsorption process. This test system is integrated with an operational system that processes a feed stream to form a product stream. The test system includes a test swing adsorption system configured to perform a swing adsorption process on the test feed stream that is based on two or more streams from different locations in the operational system. Then, passing the streams from different steps to different locations in the operational system to be recycled into the operational system.

24 Claims, 3 Drawing Sheets

(52) U.S. Cl.
CPC ......... *G01N 33/00* (2013.01); *B01D 2256/24* (2013.01); *B01D 2257/504* (2013.01); *B01D 2257/80* (2013.01); *B01D 2259/40054* (2013.01)

(58) Field of Classification Search
CPC .......... B01D 2256/24; B01D 2257/504; B01D 2257/80; B01D 2259/40054; B01D 2259/40043
USPC ........ 95/96–98, 104, 105, 117, 139; 96/109, 96/110
See application file for complete search history.

(56) References Cited

U.S. PATENT DOCUMENTS

| | | | |
|---|---|---|---|
| 3,124,152 A | 3/1964 | Payne | |
| 3,142,547 A | 7/1964 | Marsh et al. | |
| 3,508,758 A | 4/1970 | Strub | |
| 3,602,247 A | 8/1971 | Bunn et al. | |
| 3,788,036 A | 1/1974 | Lee et al. | |
| 3,967,464 A | 7/1976 | Cormier et al. | |
| 4,187,092 A | 2/1980 | Woolley | |
| 4,190,424 A * | 2/1980 | Armond | B01D 53/047 95/127 |
| 4,261,815 A | 4/1981 | Kelland | |
| 4,324,565 A | 4/1982 | Benkmann | |
| 4,325,565 A | 4/1982 | Winchell | |
| 4,329,162 A | 5/1982 | Pitcher | |
| 4,340,398 A | 7/1982 | Doshi et al. | |
| 4,386,947 A | 6/1983 | Mizuno et al. | |
| 4,445,441 A | 5/1984 | Tanca | |
| 4,461,630 A | 7/1984 | Cassidy et al. | |
| 4,496,376 A | 1/1985 | Hradek | |
| 4,705,627 A | 11/1987 | Miwa et al. | |
| 4,711,968 A | 12/1987 | Oswald et al. | |
| 4,737,170 A | 4/1988 | Searle | |
| 4,770,676 A | 9/1988 | Sircar et al. | |
| 4,783,205 A | 11/1988 | Searle | |
| 4,784,672 A | 11/1988 | Sircar | |
| 4,790,272 A | 12/1988 | Woolenweber | |
| 4,814,146 A | 3/1989 | Brand et al. | |
| 4,816,039 A | 3/1989 | Krishnamurthy et al. | |
| 4,877,429 A | 10/1989 | Hunter | |
| 4,977,745 A | 12/1990 | Heichberger | |
| 5,110,328 A | 5/1992 | Yokota et al. | |
| 5,125,934 A | 6/1992 | Krishnamurthy et al. | |
| 5,169,006 A | 12/1992 | Stelzer | |
| 5,174,796 A | 12/1992 | Davis et al. | |
| 5,224,350 A | 7/1993 | Mehra | |
| 5,234,472 A | 8/1993 | Krishnamurthy et al. | |
| 5,292,990 A | 3/1994 | Kantner et al. | |
| 5,306,331 A | 4/1994 | Auvil et al. | |
| 5,354,346 A | 10/1994 | Kumar | |
| 5,365,011 A | 11/1994 | Ramachandran et al. | |
| 5,370,728 A | 12/1994 | LaSala et al. | |
| 5,486,227 A | 1/1996 | Kumar et al. | |
| 5,547,641 A | 8/1996 | Smith et al. | |
| 5,565,018 A | 10/1996 | Baksh et al. | |
| 5,672,196 A | 9/1997 | Acharya et al. | |
| 5,700,310 A | 12/1997 | Bowman et al. | |
| 5,733,451 A | 3/1998 | Coellner et al. | |
| 5,735,938 A | 4/1998 | Baksh et al. | |
| 5,750,026 A | 5/1998 | Gadkaree et al. | |
| 5,769,928 A | 6/1998 | Leavitt | |
| 5,792,239 A | 8/1998 | Reinhold, III et al. | |
| 5,807,423 A | 9/1998 | Lemcoff et al. | |
| 5,811,616 A | 9/1998 | Holub et al. | |
| 5,827,358 A | 10/1998 | Kulish et al. | |
| 5,906,673 A | 5/1999 | Reinhold, III et al. | |
| 5,912,426 A | 6/1999 | Smolarek et al. | |
| 5,924,307 A | 7/1999 | Nenov | |
| 5,935,444 A | 8/1999 | Johnson et al. | |
| 5,968,234 A | 10/1999 | Midgett, II et al. | |
| 5,976,221 A | 11/1999 | Bowman et al. | |
| 5,997,617 A | 12/1999 | Czabala et al. | |
| 6,007,606 A | 12/1999 | Baksh et al. | |
| 6,011,192 A | 1/2000 | Baker et al. | |
| 6,023,942 A | 2/2000 | Thomas et al. | |
| 6,053,966 A | 4/2000 | Moreau et al. | |
| 6,063,161 A | 5/2000 | Keefer et al. | |
| 6,096,115 A | 8/2000 | Kleinberg | |
| 6,099,621 A | 8/2000 | Ho | |
| 6,129,780 A | 10/2000 | Millet et al. | |
| 6,136,222 A | 10/2000 | Friesen et al. | |
| 6,147,126 A | 11/2000 | DeGeorge et al. | |
| 6,152,991 A | 11/2000 | Ackley | |
| 6,156,101 A | 12/2000 | Naheiri | |
| 6,171,371 B1 | 1/2001 | Derive et al. | |
| 6,176,897 B1 | 1/2001 | Keefer | |
| 6,179,900 B1 | 1/2001 | Behling et al. | |
| 6,183,538 B1 | 2/2001 | Naheiri | |
| 6,194,079 B1 | 2/2001 | Hekal | |
| 6,210,466 B1 | 4/2001 | Whysall et al. | |
| 6,231,302 B1 | 5/2001 | Bonardi | |
| 6,245,127 B1 | 6/2001 | Kane et al. | |
| 6,284,021 B1 | 9/2001 | Lu et al. | |
| 6,311,719 B1 | 11/2001 | Hill et al. | |
| 6,345,954 B1 | 2/2002 | Al-Himyary et al. | |
| 6,398,853 B1 | 6/2002 | Keefer et al. | |
| 6,402,813 B2 | 6/2002 | Monereau et al. | |
| 6,406,523 B1 | 6/2002 | Connor et al. | |
| 6,425,938 B1 | 7/2002 | Xu et al. | |
| 6,432,379 B1 | 8/2002 | Heung | |
| 6,436,171 B1 | 8/2002 | Wang et al. | |
| 6,444,012 B1 | 9/2002 | Dolan et al. | |
| 6,444,014 B1 | 9/2002 | Mullhaupt et al. | |
| 6,444,523 B1 | 9/2002 | Fan et al. | |
| 6,451,095 B1 | 9/2002 | Keefer et al. | |
| 6,457,485 B2 | 10/2002 | Hill et al. | |
| 6,471,939 B1 | 10/2002 | Boix et al. | |
| 6,488,747 B1 | 12/2002 | Keefer | |
| 6,497,750 B2 | 12/2002 | Butwell et al. | |
| 6,500,234 B1 | 12/2002 | Ackley et al. | |
| 6,500,241 B2 | 12/2002 | Reddy | |
| 6,500,404 B1 | 12/2002 | Camblor Fernandez et al. | |
| 6,503,299 B2 | 1/2003 | Baksh et al. | |
| 6,506,351 B1 | 1/2003 | Jain et al. | |
| 6,514,318 B2 | 2/2003 | Keefer | |
| 6,514,319 B2 | 2/2003 | Keefer et al. | |
| 6,517,609 B1 | 2/2003 | Monereau et al. | |
| 6,531,516 B2 | 3/2003 | Davis et al. | |
| 6,533,846 B1 | 3/2003 | Keefer et al. | |
| 6,565,627 B1 | 5/2003 | Golden et al. | |
| 6,565,635 B2 | 5/2003 | Keefer et al. | |
| 6,565,825 B2 | 5/2003 | Ohji et al. | |
| 6,572,678 B1 | 6/2003 | Wijmans et al. | |
| 6,579,341 B2 | 6/2003 | Baker et al. | |
| 6,593,541 B1 | 7/2003 | Herren | |
| 6,595,233 B2 | 7/2003 | Pulli | |
| 6,605,136 B1 | 8/2003 | Graham et al. | |
| 6,607,584 B2 | 8/2003 | Moreau et al. | |
| 6,610,124 B1 * | 8/2003 | Dolan | B01D 53/02 95/105 |
| 6,630,012 B2 | 10/2003 | Wegeng et al. | |
| 6,631,626 B1 | 10/2003 | Hahn | |
| 6,641,645 B1 | 11/2003 | Lee et al. | |
| 6,651,645 B1 | 11/2003 | Nunez-Suarez | |
| 6,660,064 B2 | 12/2003 | Golden et al. | |
| 6,660,065 B2 | 12/2003 | Byrd et al. | |
| 6,692,626 B2 | 2/2004 | Keefer et al. | |
| 6,712,087 B2 | 3/2004 | Hill et al. | |
| 6,742,507 B2 | 6/2004 | Keefer et al. | |
| 6,746,515 B2 | 6/2004 | Wegeng et al. | |
| 6,752,852 B1 | 6/2004 | Jacksier et al. | |
| 6,770,120 B2 | 8/2004 | Neu et al. | |
| 6,773,225 B2 | 8/2004 | Yuri et al. | |
| 6,802,889 B2 | 10/2004 | Graham et al. | |
| 6,814,771 B2 | 11/2004 | Scardino et al. | |
| 6,835,354 B2 | 12/2004 | Woods et al. | |
| 6,840,985 B2 | 1/2005 | Keefer | |
| 6,866,950 B2 | 3/2005 | Connor et al. | |
| 6,889,710 B2 | 5/2005 | Wagner | |
| 6,890,376 B2 | 5/2005 | Arquin et al. | |

(56) References Cited

U.S. PATENT DOCUMENTS

| | | |
|---|---|---|
| 6,893,483 B2 | 5/2005 | Golden et al. |
| 6,902,602 B2 | 6/2005 | Keefer et al. |
| 6,916,358 B2 | 7/2005 | Nakamura et al. |
| 6,918,953 B2 | 7/2005 | Lomax, Jr. et al. |
| 6,921,597 B2 | 7/2005 | Keefer et al. |
| 6,974,496 B2 | 12/2005 | Wegeng et al. |
| 7,025,801 B2 | 4/2006 | Monereau |
| 7,027,929 B2 | 4/2006 | Wang |
| 7,029,521 B2 | 4/2006 | Johansson |
| 7,074,323 B2 | 7/2006 | Ghijsen |
| 7,077,891 B2 | 7/2006 | Jaffe et al. |
| 7,087,331 B2 | 8/2006 | Keefer et al. |
| 7,094,275 B2 | 8/2006 | Keefer et al. |
| 7,097,925 B2 | 8/2006 | Keefer et al. |
| 7,112,239 B2 | 9/2006 | Kimbara et al. |
| 7,117,669 B2 | 10/2006 | Kaboord et al. |
| 7,122,073 B1 | 10/2006 | Notaro et al. |
| 7,128,775 B2 | 10/2006 | Celik et al. |
| 7,144,016 B2 | 12/2006 | Gozdawa |
| 7,160,356 B2 | 1/2007 | Koros et al. |
| 7,160,367 B2 | 1/2007 | Babicki et al. |
| 7,166,149 B2 | 1/2007 | Dunne et al. |
| 7,172,645 B1 | 2/2007 | Pfister et al. |
| 7,189,280 B2 | 3/2007 | Alizadeh-Khiavi et al. |
| 7,250,073 B2 | 7/2007 | Keefer et al. |
| 7,250,074 B2 | 7/2007 | Tonkovich et al. |
| 7,255,727 B2 | 8/2007 | Monereau et al. |
| 7,258,725 B2 | 8/2007 | Ohmi et al. |
| 7,276,107 B2 | 10/2007 | Baksh et al. |
| 7,279,029 B2 | 10/2007 | Occhialini et al. |
| 7,285,350 B2 | 10/2007 | Keefer et al. |
| 7,297,279 B2 | 11/2007 | Johnson et al. |
| 7,311,763 B2 | 12/2007 | Neary |
| RE40,006 E | 1/2008 | Keefer et al. |
| 7,314,503 B2 | 1/2008 | Landrum et al. |
| 7,354,562 B2 | 4/2008 | Ying et al. |
| 7,387,849 B2 | 6/2008 | Keefer et al. |
| 7,390,350 B2 | 6/2008 | Weist, Jr. et al. |
| 7,404,846 B2 | 7/2008 | Golden et al. |
| 7,438,079 B2 | 10/2008 | Cohen et al. |
| 7,449,049 B2 | 11/2008 | Thomas et al. |
| 7,456,131 B2 | 11/2008 | Klett et al. |
| 7,510,601 B2 | 3/2009 | Whitley et al. |
| 7,527,670 B2 | 5/2009 | Ackley et al. |
| 7,553,568 B2 | 6/2009 | Keefer |
| 7,578,864 B2 | 8/2009 | Watanabe et al. |
| 7,604,682 B2 | 10/2009 | Seaton |
| 7,637,989 B2 | 12/2009 | Bong |
| 7,641,716 B2 | 1/2010 | Lomax, Jr. et al. |
| 7,645,324 B2 | 1/2010 | Rode et al. |
| 7,651,549 B2 | 1/2010 | Whitley |
| 7,674,319 B2 | 3/2010 | Lomax, Jr. et al. |
| 7,674,539 B2 | 3/2010 | Keefer et al. |
| 7,687,044 B2 | 3/2010 | Keefer et al. |
| 7,713,333 B2 | 5/2010 | Rege et al. |
| 7,717,981 B2 | 5/2010 | LaBuda et al. |
| 7,722,700 B2 | 5/2010 | Sprinkle |
| 7,731,782 B2 | 6/2010 | Kelley et al. |
| 7,740,687 B2 | 6/2010 | Reinhold, III |
| 7,744,676 B2 | 6/2010 | Leitmayr et al. |
| 7,744,677 B2 | 6/2010 | Barclay et al. |
| 7,758,051 B2 | 7/2010 | Roberts-Haritonov et al. |
| 7,758,988 B2 | 7/2010 | Keefer et al. |
| 7,763,098 B2 | 7/2010 | Alizadeh-Khiavi et al. |
| 7,763,099 B2 | 7/2010 | Verma et al. |
| 7,792,983 B2 | 9/2010 | Mishra et al. |
| 7,793,675 B2 | 9/2010 | Cohen et al. |
| 7,806,965 B2 | 10/2010 | Stinson |
| 7,819,948 B2 | 10/2010 | Wagner |
| 7,828,877 B2 | 11/2010 | Sawada et al. |
| 7,828,880 B2 | 11/2010 | Moriya et al. |
| 7,854,793 B2 | 12/2010 | Rarig et al. |
| 7,858,169 B2 | 12/2010 | Yamashita |
| 7,862,645 B2 | 1/2011 | Whitley et al. |
| 7,867,320 B2 | 1/2011 | Baksh et al. |
| 7,902,114 B2 | 3/2011 | Bowie et al. |
| 7,938,886 B2 | 5/2011 | Hershkowitz et al. |
| 7,947,118 B2 | 5/2011 | Rarig et al. |
| 7,947,120 B2 | 5/2011 | Deckman et al. |
| 7,959,720 B2 | 6/2011 | Deckman et al. |
| 8,016,918 B2 | 9/2011 | LaBuda et al. |
| 8,034,164 B2 | 10/2011 | Lomax, Jr. et al. |
| 8,071,063 B2 | 12/2011 | Reyes et al. |
| 8,128,734 B2 | 3/2012 | Song |
| 8,142,745 B2 | 3/2012 | Reyes et al. |
| 8,142,746 B2 | 3/2012 | Reyes et al. |
| 8,192,709 B2 | 6/2012 | Reyes et al. |
| 8,210,772 B2 | 7/2012 | Gillecriosd |
| 8,227,121 B2 | 7/2012 | Adams et al. |
| 8,262,773 B2 | 9/2012 | Northrop et al. |
| 8,262,783 B2 | 9/2012 | Stoner et al. |
| 8,268,043 B2 | 9/2012 | Celik et al. |
| 8,268,044 B2 | 9/2012 | Wright et al. |
| 8,272,401 B2 | 9/2012 | McLean |
| 8,287,629 B2 | 10/2012 | Fujita et al. |
| 8,319,090 B2 | 11/2012 | Kitamura |
| 8,337,594 B2 | 12/2012 | Corma Canos et al. |
| 8,361,200 B2 | 1/2013 | Sayari et al. |
| 8,361,205 B2 | 1/2013 | Desai et al. |
| 8,377,173 B2 | 2/2013 | Chuang |
| 8,444,750 B2 | 5/2013 | Deckman et al. |
| 8,470,395 B2 | 6/2013 | Khiavi et al. |
| 8,480,795 B2 | 7/2013 | Siskin et al. |
| 8,512,569 B2 | 8/2013 | Eaton et al. |
| 8,518,356 B2 | 8/2013 | Schaffer et al. |
| 8,529,662 B2 | 9/2013 | Kelley et al. |
| 8,529,663 B2 | 9/2013 | Reyes et al. |
| 8,529,664 B2 | 9/2013 | Deckman et al. |
| 8,529,665 B2 | 9/2013 | Manning et al. |
| 8,535,414 B2 | 9/2013 | Johnson et al. |
| 8,545,602 B2 | 10/2013 | Chance et al. |
| 8,551,444 B2 | 10/2013 | Agnihotri et al. |
| 8,573,124 B2 | 11/2013 | Havran et al. |
| 8,591,627 B2 | 11/2013 | Jain |
| 8,591,634 B2 | 11/2013 | Winchester et al. |
| 8,616,233 B2 | 12/2013 | McLean et al. |
| 8,657,922 B2 | 2/2014 | Yamawaki et al. |
| 8,673,059 B2 | 3/2014 | Leta et al. |
| 8,680,344 B2 | 3/2014 | Weston et al. |
| 8,715,617 B2 | 5/2014 | Genkin et al. |
| 8,752,390 B2 | 6/2014 | Wright et al. |
| 8,778,051 B2 | 7/2014 | Weist, Jr. et al. |
| 8,784,533 B2 | 7/2014 | Leta et al. |
| 8,784,534 B2 | 7/2014 | Kamakoti et al. |
| 8,784,535 B2 | 7/2014 | Ravikovitch et al. |
| 8,795,411 B2 | 8/2014 | Hufton et al. |
| 8,808,425 B2 | 8/2014 | Genkin et al. |
| 8,808,426 B2 | 8/2014 | Sundaram |
| 8,814,985 B2 | 8/2014 | Gerds et al. |
| 8,852,322 B2 | 10/2014 | Gupta et al. |
| 8,858,683 B2 | 10/2014 | Deckman |
| 8,875,483 B2 | 11/2014 | Wettstein |
| 8,906,138 B2 | 12/2014 | Rasmussen et al. |
| 8,921,637 B2 | 12/2014 | Sundaram et al. |
| 8,939,014 B2 | 1/2015 | Kamakoti et al. |
| 9,005,561 B2 | 4/2015 | Leta |
| 9,017,457 B2 | 4/2015 | Tammera |
| 9,028,595 B2 | 5/2015 | Sundaram et al. |
| 9,034,078 B2 | 5/2015 | Wanni et al. |
| 9,034,079 B2 | 5/2015 | Deckman et al. |
| 9,050,553 B2 | 6/2015 | Alizadeh-Khiavi et al. |
| 9,067,168 B2 | 6/2015 | Frederick et al. |
| 9,095,809 B2 | 8/2015 | Deckman et al. |
| 9,108,145 B2 | 8/2015 | Kalbassi et al. |
| 9,120,049 B2 | 9/2015 | Sundaram et al. |
| 9,126,138 B2 | 9/2015 | Deckman et al. |
| 9,162,175 B2 | 10/2015 | Sundaram |
| 9,168,485 B2 | 10/2015 | Deckman et al. |
| 2001/0047824 A1 | 12/2001 | Hill et al. |
| 2002/0124885 A1 | 9/2002 | Hill et al. |
| 2002/0162452 A1 | 11/2002 | Butwell et al. |
| 2003/0075485 A1 | 4/2003 | Ghijsen |
| 2003/0129101 A1 | 7/2003 | Zettel |
| 2003/0131728 A1 | 7/2003 | Kanazirev et al. |

(56) References Cited

U.S. PATENT DOCUMENTS

| | | |
|---|---|---|
| 2003/0170527 A1 | 9/2003 | Finn et al. |
| 2003/0202918 A1 | 10/2003 | Ashida et al. |
| 2003/0205130 A1 | 11/2003 | Neu et al. |
| 2003/0223856 A1 | 12/2003 | Yuri et al. |
| 2004/0099142 A1 | 5/2004 | Arquin et al. |
| 2004/0118277 A1 | 6/2004 | Kim |
| 2004/0197596 A1 | 10/2004 | Connor et al. |
| 2004/0232622 A1 | 11/2004 | Gozdawa |
| 2005/0066815 A1* | 3/2005 | Krushnevych ..... B01D 53/1475 96/108 |
| 2005/0109419 A1 | 5/2005 | Ohmi et al. |
| 2005/0114032 A1 | 5/2005 | Wang |
| 2005/0129952 A1 | 6/2005 | Sawada et al. |
| 2005/0014511 A1 | 7/2005 | Keefer et al. |
| 2005/0145111 A1 | 7/2005 | Keefer et al. |
| 2005/0150378 A1 | 7/2005 | Dunne et al. |
| 2005/0229782 A1 | 10/2005 | Monereau et al. |
| 2005/0252378 A1 | 11/2005 | Celik et al. |
| 2006/0048648 A1 | 3/2006 | Gibbs et al. |
| 2006/0049102 A1 | 3/2006 | Miller et al. |
| 2006/0076270 A1 | 4/2006 | Poshusta et al. |
| 2006/0099096 A1 | 5/2006 | Shaffer et al. |
| 2006/0105158 A1 | 5/2006 | Fritz et al. |
| 2006/0162556 A1 | 7/2006 | Ackley et al. |
| 2006/0165574 A1 | 7/2006 | Sayari |
| 2006/0169142 A1 | 8/2006 | Rode et al. |
| 2006/0236862 A1 | 10/2006 | Golden et al. |
| 2007/0084241 A1 | 4/2007 | Kretchmer et al. |
| 2007/0084344 A1 | 4/2007 | Moriya et al. |
| 2007/0222160 A1 | 9/2007 | Roberts-Haritonov et al. |
| 2007/0253872 A1 | 11/2007 | Keefer et al. |
| 2007/0261550 A1 | 11/2007 | Ota |
| 2007/0261557 A1 | 11/2007 | Gadkaree et al. |
| 2007/0283807 A1 | 12/2007 | Whitley |
| 2008/0051279 A1 | 2/2008 | Klett et al. |
| 2008/0072822 A1 | 3/2008 | White |
| 2008/0128655 A1 | 6/2008 | Garg et al. |
| 2008/0282883 A1 | 11/2008 | Rarig et al. |
| 2008/0282884 A1 | 11/2008 | Kelley et al. |
| 2008/0282885 A1 | 11/2008 | Deckman et al. |
| 2008/0282886 A1 | 11/2008 | Reyes et al. |
| 2008/0282887 A1 | 11/2008 | Chance |
| 2008/0282892 A1 | 11/2008 | Deckman et al. |
| 2008/0289497 A1 | 11/2008 | Barclay et al. |
| 2008/0307966 A1 | 12/2008 | Stinson |
| 2008/0314550 A1 | 12/2008 | Greco |
| 2009/0004073 A1 | 1/2009 | Gleize et al. |
| 2009/0014902 A1 | 1/2009 | Koivunen et al. |
| 2009/0025553 A1 | 1/2009 | Keefer et al. |
| 2009/0037550 A1 | 2/2009 | Mishra et al. |
| 2009/0071333 A1 | 3/2009 | LaBuda et al. |
| 2009/0079870 A1 | 3/2009 | Matsui |
| 2009/0107332 A1 | 4/2009 | Wagner |
| 2009/0151559 A1 | 6/2009 | Verma et al. |
| 2009/0162268 A1 | 6/2009 | Hufton et al. |
| 2009/0180423 A1 | 7/2009 | Kroener |
| 2009/0241771 A1 | 10/2009 | Manning et al. |
| 2009/0284013 A1 | 11/2009 | Anand et al. |
| 2009/0308248 A1 | 12/2009 | Siskin et al. |
| 2009/0314159 A1 | 12/2009 | Haggerty |
| 2010/0059701 A1 | 3/2010 | McLean |
| 2010/0077920 A1 | 4/2010 | Baksh et al. |
| 2010/0089241 A1 | 4/2010 | Stoner et al. |
| 2010/0186445 A1 | 7/2010 | Minta et al. |
| 2010/0212493 A1 | 8/2010 | Rasmussen et al. |
| 2010/0251887 A1 | 10/2010 | Jain |
| 2010/0252497 A1 | 10/2010 | Ellison et al. |
| 2010/0263534 A1 | 10/2010 | Chuang |
| 2010/0282593 A1 | 11/2010 | Speirs et al. |
| 2010/0288704 A1 | 11/2010 | Amsden et al. |
| 2011/0031103 A1 | 2/2011 | Deckman et al. |
| 2011/0067440 A1 | 3/2011 | Van Aken |
| 2011/0067770 A1 | 3/2011 | Pederson et al. |
| 2011/0146494 A1 | 6/2011 | Desai et al. |
| 2011/0217218 A1 | 9/2011 | Gupta et al. |
| 2011/0277620 A1 | 11/2011 | Havran et al. |
| 2011/0291051 A1 | 12/2011 | Hershkowitz et al. |
| 2011/0296871 A1 | 12/2011 | Van Soest-Vercammen et al. |
| 2011/0308524 A1 | 12/2011 | Brey et al. |
| 2012/0024152 A1 | 2/2012 | Yamawaki et al. |
| 2012/0031144 A1 | 2/2012 | Northrop et al. |
| 2012/0067216 A1 | 3/2012 | Corma-Canos et al. |
| 2012/0152115 A1 | 6/2012 | Gerds et al. |
| 2012/0222551 A1 | 9/2012 | Deckman |
| 2012/0222552 A1 | 9/2012 | Ravikovitch et al. |
| 2012/0222553 A1 | 9/2012 | Kamakoti et al. |
| 2012/0222554 A1 | 9/2012 | Leta et al. |
| 2012/0222555 A1 | 9/2012 | Gupta et al. |
| 2012/0255377 A1 | 10/2012 | Kamakoti et al. |
| 2012/0308456 A1 | 12/2012 | Leta et al. |
| 2012/0312163 A1 | 12/2012 | Leta et al. |
| 2013/0061755 A1 | 3/2013 | Frederick et al. |
| 2013/0225898 A1 | 8/2013 | Sundaram et al. |
| 2014/0013955 A1 | 1/2014 | Tammera et al. |
| 2014/0060326 A1 | 3/2014 | Sundaram et al. |
| 2014/0157986 A1 | 6/2014 | Ravikovitch et al. |
| 2014/0208797 A1 | 7/2014 | Kelley et al. |
| 2014/0216254 A1 | 8/2014 | Tammera et al. |
| 2015/0013377 A1 | 1/2015 | Oelfke |
| 2015/0068397 A1 | 3/2015 | Boulet et al. |
| 2015/0196870 A1 | 7/2015 | Albright et al. |
| 2015/0328578 A1 | 11/2015 | Deckman et al. |
| 2016/0023155 A1 | 1/2016 | Ramkumar et al. |
| 2016/0129433 A1 | 5/2016 | Tammera et al. |
| 2016/0166972 A1 | 6/2016 | Owens et al. |
| 2016/0236135 A1 | 8/2016 | Tammera et al. |
| 2016/0332105 A1 | 11/2016 | Tammera et al. |
| 2016/0332106 A1 | 11/2016 | Tammera et al. |
| 2017/0056810 A1 | 3/2017 | Johnson et al. |
| 2017/0056813 A1 | 3/2017 | McMahon et al. |
| 2017/0056814 A1 | 3/2017 | Marshall et al. |
| 2017/0056815 A1 | 3/2017 | Smith et al. |
| 2017/0113173 A1 | 4/2017 | Fowler et al. |
| 2017/0113175 A1 | 4/2017 | Fowler et al. |
| 2017/0113176 A1 | 4/2017 | Fowler et al. |

FOREIGN PATENT DOCUMENTS

| | | |
|---|---|---|
| EP | 0225736 | 6/1987 |
| EP | 0257493 | 2/1988 |
| EP | 0262934 | 4/1988 |
| EP | 0426937 | 5/1991 |
| EP | 1018359 | 7/2000 |
| EP | 1045728 | 11/2000 |
| EP | 1577561 | 9/2005 |
| EP | 1674555 | 6/2006 |
| EP | 2823872 | 1/2015 |
| FR | 2924951 | 6/2009 |
| JP | 58-114715 | 7/1983 |
| JP | 59-232174 | 12/1984 |
| JP | 60-189318 | 12/1985 |
| JP | 2002-253818 | 10/1990 |
| JP | 04-180978 | 6/1992 |
| JP | 2011-169640 | 6/1999 |
| JP | 2011-280921 | 10/1999 |
| JP | 2000-024445 | 8/2001 |
| JP | 2002-348651 | 12/2002 |
| JP | 2006-016470 | 1/2006 |
| JP | 2006-036849 | 2/2006 |
| JP | 2008-272534 | 11/2008 |
| WO | WO2002/024309 | 3/2002 |
| WO | WO2002/073728 | 9/2002 |
| WO | WO2005/090793 | 9/2005 |
| WO | WO2011/139894 | 11/2011 |

OTHER PUBLICATIONS

U.S. Appl. No. 15/450,618, filed Mar. 6, 2017, Tammera et al.
ExxonMobil Research and Engineering and QuestAir (2008) "A New Commercialized Process for Lower Cost H2 Recovery—Rapid Cycle Pressure Swing Adsorption (RCPSA)," *Brochure*, 4 pgs.
Farooq, S. et al. (1990) "Continuous Countercurrent Flow Model for a Bulk PSA Separation Process," *AIChE J.*, v36 (2) p. 310-314.

(56) References Cited

OTHER PUBLICATIONS

FlowServe (2005)"Exceeding Expectations, US Navy Cuts Maintenance Costs With Flowserve GX-200 Non-Contacting Seal Retrofits," *Face-to-Face*, v17.1, 8 pgs.

GE Oil & Gas (2007) "Dry Gas Seal Retrofit," Florene, Italy, www.ge.com/oilandgas. 4 pgs.

Hopper, B. et al. (2008) "World's First 10,000 psi Sour Gas Injection Compressor," *Proceedings of the 37$^{th}$ Turbomachinery Symosium*, pp. 73-95.

Kikkinides, E. S. et al. (1995) "Natural Gas Desulfurization by Adsorption: Feasibility and Multiplicity of Cyclic Steady States," *Ind. Eng. Chem. Res*. V. 34, pp. 255-262.

Rameshni, Mahin (May 19, 2007) "Strategies for Sour Gas Field Developments," *Worley Parsons-Brochure*, 20 pgs.

Reyes, S. C. et al. (1997) "Frequency Modulation Methods for Diffusion and Adsorption Measurements in Porous Solids," *J. Phys. Chem. B*. v101, pp. 614-622.

Ruthven, D. M. et al. (1996) "Performance of a Parallel Passage Adsorbent Contactor," *Gas. Sep. Purif.*, vol. 10, No. 1, pp. 63-73.

Stahley, J. S. (2003) "Design, Operation, and Maintenance Considerations for Improved Dry Gas Seal Realiability in Centrifugal Compressors," *Dresser-Rand, Tech. Paper* 134, 15 pages.

Suzuki, M. (1985) "Continuous-Countercurrent-Flow Approximation for Dynamic Steady State Profile of Pressure Swing Adsorption" *AIChE Symp. Ser*. v81 (242) pp. 67-73.

\* cited by examiner

APPARATUS AND SYSTEM FOR TESTING SWING ADSORPTION PROCESSES

CROSS-REFERENCE TO RELATED APPLICATION

This application claims the benefit of U.S. Provisional Patent Application 62/401,435, filed Sep. 29, 2016, entitled APPARATUS AND SYSTEM FOR TESTING SWING ADSORPTION PROCESSES, the entirety of which is incorporated by reference herein.

FIELD

The present techniques relate to a system associated with an enhanced swing adsorption process. In particular, the system relates to testing a swing adsorption process for removal of contaminants from a feed stream utilizing adsorbent beds to enhance recovery of hydrocarbons.

BACKGROUND

Gas separation is useful in many industries and can typically be accomplished by flowing a mixture of gases over an adsorbent material that preferentially adsorbs one or more gas components, while not adsorbing one or more other gas components. The non-adsorbed components are recovered as a separate product.

One particular type of gas separation technology is swing adsorption, such as temperature swing adsorption (TSA), pressure swing adsorption (PSA), partial pressure purge swing adsorption (PPSA), rapid cycle pressure swing adsorption (RCPSA), rapid cycle partial pressure swing adsorption (RCPPSA), and not limited to but also combinations of the fore mentioned processes, such as pressure and temperature swing adsorption. As an example, PSA processes rely on the phenomenon of gases being more readily adsorbed within the pore structure or free volume of an adsorbent material when the gas is under pressure. That is, the higher the gas pressure, the greater the amount of readily-adsorbed gas adsorbed. When the pressure is reduced, the adsorbed component is released, or desorbed from the adsorbent material.

The swing adsorption processes (e.g., PSA and TSA) may be used to separate gases of a gas mixture because different gases tend to fill the micropore of the adsorbent material to different extents. For example, if a gas mixture, such as natural gas, is passed under pressure through a vessel containing an adsorbent material that is more selective towards carbon dioxide than it is for methane, at least a portion of the carbon dioxide is selectively adsorbed by the adsorbent material, and the gas exiting the vessel is enriched in methane. When the adsorbent material reaches the end of its capacity to adsorb carbon dioxide, it is regenerated in a PSA process, for example, by reducing the pressure, thereby releasing the adsorbed carbon dioxide. The adsorbent material is then typically purged and repressurized. Then, the adsorbent material is ready for another adsorption cycle.

The swing adsorption processes typically involve one or more adsorbent bed units, which include adsorbent beds disposed within a housing configured to maintain fluids at various pressures for different steps in an adsorption cycle within the unit. These adsorbent bed units utilize different packing material in the bed structures. For example, the adsorbent bed units utilize checker brick, pebble beds or other available packing. As an enhancement, some adsorbent bed units may utilize engineered packing within the bed structure. The engineered packing may include a material provided in a specific configuration, such as a honeycomb, ceramic forms or the like.

Further, various adsorbent bed units may be coupled together with conduits and valves to manage the flow of fluids. Orchestrating these adsorbent bed units involves coordinating the cycles for each adsorbent bed unit with other adsorbent bed units in the system. A complete PSA cycle can vary from seconds to minutes as it transfers a plurality of gaseous streams through one or more of the adsorbent bed units.

For conventional bench-top laboratory scale facilities, flow streams are typically provided by blending fluids stored in storage vessels. While this may provide a representative flow stream for testing, it limits the size of the test unit and test system. Furthermore, such facilities require a significant amount of time to set-up and operate and the various product streams from testing may not be recovered. To collect the necessary information to facilitate scale-up, it may be necessary to analyze and test technology at a scale that is representative of large commercial applications. Such facilities may be too large for laboratory scale evaluation.

Accordingly, there remains a need in the industry for apparatus, methods, and systems that provide enhancements in testing swing adsorption systems. The present techniques provide enhancements by integrating swing adsorption processes to separate contaminants from a feed stream with operational gas processing systems. This facilitates operation at a sufficiently large scale to facilitate scale-up to large commercial facilities, while minimizing or eliminating any lost fluid inventories. The present techniques overcome the drawbacks of conventional testing approaches based on this integration.

SUMMARY OF THE INVENTION

In one embodiment, the present techniques describe a cyclical swing adsorption process for removing contaminants from a feed stream. The process comprising: performing a process to remove one or more contaminants from a feed stream in an operational system; separating one or more streams in the process of the operational system to form a test feed stream; passing the test feed stream to a test system, wherein the test system performs two or more steps in a cycle to perform one or more swing adsorption processes on the test feed stream to remove one or more contaminants from the test feed stream to form a test product stream and a test purge product stream; and mixing at least a portion of the test product stream and the test purge product stream with the streams in the operational system.

In other embodiments, various enhancements may be included. The cyclical swing adsorption process may include wherein the one or more swing adsorption processes comprises: a) performing one or more adsorption steps, wherein each of the adsorption steps comprises passing the test feed stream from the operational system through the test swing adsorption system to remove one or more contaminants from the test feed stream and to form a test product stream; b) performing one or more purge steps, wherein each of the purge steps comprise passing a test purge stream through the test swing adsorption system to form a test purge product stream; and c) repeating the steps a) to b) for at least one additional cycle. Further, the cyclical swing adsorption process may include the test purge stream is provided in a counter flow direction relative to the flow of the test feed stream; wherein the one or more contaminants comprise water; wherein the one or more contaminants comprise $CO_2$;

wherein the cycle duration is greater than 1 second and less than 600 seconds or is greater than 2 seconds and less than 300 seconds; wherein the feed stream is a hydrocarbon containing stream having greater than one volume percent hydrocarbons based on the total volume of the feed stream; wherein the feed pressure is in the range between 400 pounds per square inch absolute (psia) and 1,400 psia; blending two or more streams from different locations in the process of the operational system to form the test feed stream; wherein each of the two or more streams have different stream compositions; adjusting temperature of the blended stream; increasing pressure of the blended stream prior to passing the test stream to the test system; wherein the operational system is configured to remove one or more contaminants to a pipeline specification, while the test system is configured to remove contaminants to a cryogenic specification; and/or communicating with one or more sensors and/or one or more control valves to manage one of the flow rate, composition, temperature, pressure and any combination thereof within the different streams of the test system. Also, the process may include performing a second swing adsorption process in the test system further comprising: i) performing one or more acid adsorption steps, wherein each of the acid adsorption steps comprises passing a portion of the test product stream from the test swing adsorption system through a second swing adsorption system to remove acid gas from the portion of the test product stream and form a second test product stream; ii) performing one or more acid purge steps, wherein each of the acid purge steps comprises passing a portion of the test product stream through the second swing adsorption system to form a second test purge product stream; and iii) repeating the steps i) to ii) for at least one additional cycle.

In yet another embodiment, the present techniques describe a system for testing swing adsorption processes for removing contaminants from a test feed stream. The system include: an operational system configured to perform a process to remove one or more contaminants from a feed stream; a test system in fluid communication with the operational system and comprising: one or more separation units in fluid communication with the operational system and configured to separate one or more streams from the operational system to form a test feed stream; a swing adsorption system comprising one or more adsorbent bed units, wherein each of the one or more adsorbent bed units is configured to separate contaminants from a test feed stream and to output a test product stream in an adsorption step; a recycle unit configured to receive the test product stream and pass at least a portion of the test product stream to one of the one or more adsorbent bed units to perform a purge step and form a test purge product stream; and one or more conduits configured to pass the test product stream and the test purge product stream to operational system.

In still yet other embodiments, various enhancements are described. The system may further comprise a blending unit in fluid communication with the one or more separation units and configured to blend two or more streams from different locations in the operational system to form the test feed stream; wherein the test system further comprises: a second swing adsorption system comprising one or more second adsorbent bed units, wherein each of the one or more second adsorbent bed units is configured to separate a second contaminant from the at least a portion of the test product stream in an adsorption step, wherein the second contaminant is different from the contaminants; a recycle unit configured to receive the second test product stream and pass at least a portion of the second test product stream to one of the one or more second adsorbent bed units to perform a second purge step and form a second test purge product stream; and one or more conduits configured to pass the second test product stream and the second test purge product stream to operational system; and/or wherein the swing adsorption system is configured to operate on a cycle duration greater than 1 second and less than 600 seconds or greater than 2 seconds and less than 300 seconds. In addition, the system may further comprise a control unit configured to: obtain one of operation conditions or flow rate; calculate the flow rates for the respective streams based on a preferred composition of the blended stream; and calculate any adjustments to pressure and/or temperature in the blended stream; may include one or more sensors configured to measure the operation conditions on the respective streams and to communicate the operation conditions to the control unit; and/or may further comprise one or more flow control mechanisms configured to adjust the flow rate for the respective stream and to communicate the flow rate to the control unit.

In a further embodiment, a process for removing contaminants from a feed stream and testing one or more swing adsorption processes is described. The process may comprise: performing a process to remove one or more contaminants from a feed stream in an operational system to form a process product stream; separating one or more streams in the process from the operational system to form a test feed stream; passing the test feed stream to a test system, performing one or more swing adsorption processes on the test feed stream in the test system to remove one or more test contaminants from the test feed stream to form a test product stream having less test contaminants than the test feed stream and a test purge product stream containing at least a portion of the one or more test contaminants; mixing at least a portion of the test product stream a first stream in the operational system prior to the forming the process product stream; and mixing at least a portion of the test purge product stream with a second stream in the operational system prior to the forming the process product stream.

In a yet another embodiment, a system for testing one or more swing adsorption processes associated with an operational system is described. The system may include: an operational system configured to perform a process to remove one or more contaminants from a feed stream to form a process product stream; a test system in fluid communication with the operational system and comprising: one or more separation units in fluid communication with the operational system and configured to separate one or more streams from the operational system to form a test feed stream; a swing adsorption system comprising one or more adsorbent bed units, wherein each of the one or more adsorbent bed units is configured to receive the test feed stream in an adsorption step and to separate test contaminants from the test feed stream and to output a test product stream having less test contaminants than the test feed stream; a recycle unit in fluid communication with the swing adsorption system and configured to receive the test product stream and to pass at least a portion of the test product stream to one of the one or more adsorbent bed units in a purge step and form a test purge product stream; and one or more conduits configured to pass the test product stream to the operational system and to pass the test purge product stream to the operational system.

BRIEF DESCRIPTION OF THE FIGURES

The foregoing and other advantages of the present disclosure may become apparent upon reviewing the following detailed description and drawings of non-limiting examples of embodiments.

DETAILED DESCRIPTION OF THE INVENTION

Figure 1:
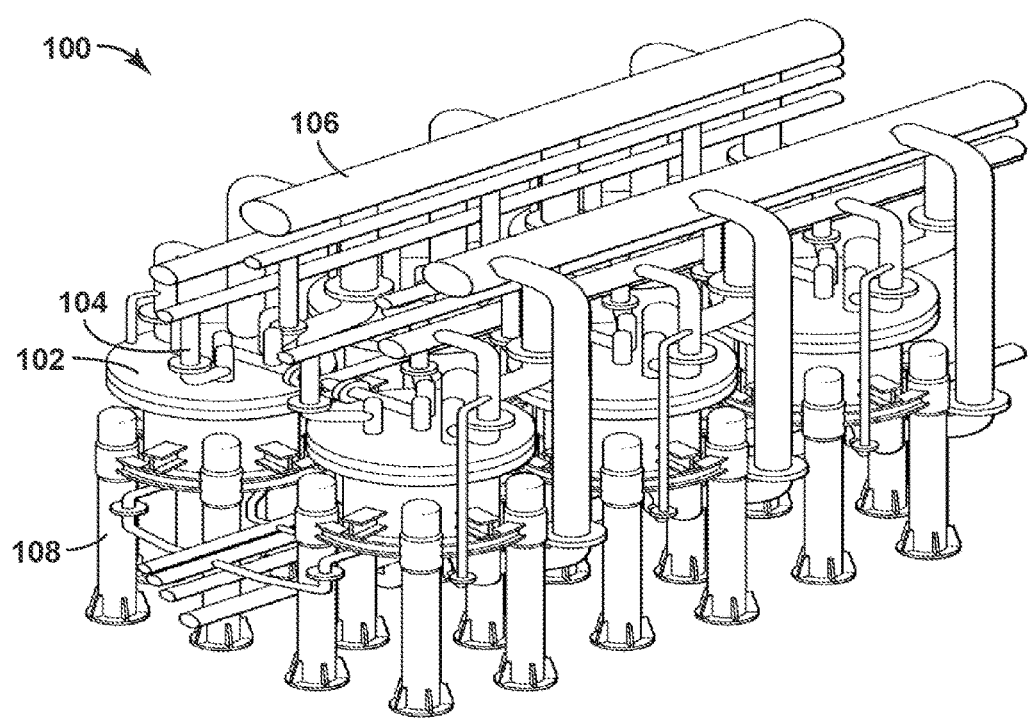
FIG. 1 is a three-dimensional diagram of the swing adsorption system with six adsorbent bed units and interconnecting piping in accordance with an embodiment of the present techniques.

Unless otherwise explained, all technical and scientific terms used herein have the same meaning as commonly understood by one of ordinary skill in the art to which this disclosure pertains. The singular terms "a," "an," and "the" include plural referents unless the context clearly indicates otherwise. Similarly, the word "or" is intended to include "and" unless the context clearly indicates otherwise. The term "includes" means "comprises." All patents and publications mentioned herein are incorporated by reference in their entirety, unless otherwise indicated. In case of conflict as to the meaning of a term or phrase, the present specification, including explanations of terms, control. Directional terms, such as "upper," "lower," "top," "bottom," "front," "back," "vertical," and "horizontal," are used herein to express and clarify the relationship between various elements. It should be understood that such terms do not denote absolute orientation (e.g., a "vertical" component can become horizontal by rotating the device). The materials, methods, and examples recited herein are illustrative only and not intended to be limiting.

As used herein, "stream" refers to fluid (e.g., solids, liquid and/or gas) being conducted through various equipment. The equipment may include conduits, vessels, manifolds, units or other suitable devices.

As used herein, volume percent is based on standard conditions. The standard conditions for a method may be normalized to the temperature of 0° C. (e.g., 32° F.) and absolute pressure of 100 kiloPascals (kPa) (1 bar).

As used herein, "conduit" refers to a tubular member forming a channel through which fluids or the other materials are conveyed. The conduit may include one or more of a pipe, a manifold, a tube or the like.

The present techniques relate to a swing adsorption process (e.g., a rapid cycle process) for the removal of one of more contaminants from a feed stream. In particular, the present techniques involve a testing configuration that may be used with an existing processing system to collect information to facilitate scale-up to large commercial applications. That is, this configuration may be used to perform field trials to conduct detailed fundamental measurements and research, while being representative of a commercial applications, thereby increasing the confidence on scale-up and lessening problems with the commercial applications.

The present techniques provide a mechanism or configuration to test the performance of a new swing adsorption processes and technology within an operational system (e.g., an existing production facility) without upsetting the performance of the operational system. To test the performance of the swing adsorption technology at multiple operating points, the configuration involves several fluid connection pathways (e.g., valves and conduits) to the operational system at different locations or different stages of gas purification. The fluid connection pathways provide a mechanism to create a blended composition for a desired test condition (e.g., a predetermined test composition). In such configuration, gas stream from one or more source locations in the operational system may be blended to provide a stream that contains the desired amount of contaminants (e.g., test contaminants, such as $H_2O$ and $CO_2$). The blended stream may be treated before passing the test feed stream to the test system, which may include a new configuration or technology. Once the test feed stream is processed by the test system, the test product stream (e.g., resulting product streams) and/or test waste streams (e.g., resulting purge product streams, resulting blowdown streams and/or resulting depressurization streams) are passed back into the operational system. The produced streams from the test system may be recycled upstream of the inlet fluid pathway locations to provide a recycle within the operational system that maintains a stable concentration and flowrate. Returning the resulting test streams from the test system to specific locations within the operational system (e.g., upstream of the locations where the respective streams are removed from the operational system) manages the operational systems production (e.g., lessening off-specification product) even if the new technology does not behave as predicted. As both the test system product and waste streams are recycled back to the operational system, the flowrate and composition of the streams may be stable as long as the feed rate to the test system is steady. Depending on the state of the test stream(s) that are conducted away from the test system (e.g., operation conditions, such as pressure, temperature and/or composition), the return locations of these streams may be selected to utilize the spare capacity of existing equipment. The test product streams and/or test waste gas streams, such as test purge streams, may be compressed to the desired pressure and/or existing compression may be used for the duration of test phase or testing operations.

In addition, the test system may include a control system, which includes various equipment to monitor and control the streams and/or test swing adsorption processes. For example, a control unit may be utilized to communicate with one or more sensors and/or one or more control valves to manage the flow rate, composition, temperature and pressure within the different streams of the test system. The equipment may regulate flow of specific streams to specific locations in the test system at desired operating conditions (e.g., pressure, temperature and any combination thereof). Also, the equipment may regulate the flow streams returning back to the operational system, such that overall operation is stable. The instrumentation or equipment may include temperature sensors, pressure sensors, flow rate monitors and/or variable control valves. For example, a control system may be configured to regulate several control valves, which are configured to control the flow of streams from the operational system or facility, such that the test system or facility receives a test feed stream at a desired flow rate and composition. The control system may be further configured to distribute the test feed stream to various locations in the test system and return the resulting product streams and waste streams to the operational facility to maintain stable operation.

The test system may include one or more adsorbent bed units to perform a swing adsorption process or groups of adsorbent bed unit configured to perform a series of swing adsorption processes. Each adsorbent bed unit is configured to perform a specific cycle, which may include an adsorption step and a regeneration step (e.g., a purge step). By way of example, the steps may include one or more feed steps, one or more depressurization steps, one or more purge steps, one or more recycle steps, and one or more re-pressurization steps. The adsorption step may involve passing a feed stream through the adsorbent bed to remove contaminants (e.g., test contaminants) from the test feed stream. The regeneration step may include one or more purge steps, one or more blowdown steps, one or more heating steps and/or one or more repressurization steps.

Further, various enhancements may be provided in certain embodiments. For example, the purge stream may be heated within the test system prior to passing through the swing adsorption system. The purge stream may be heated by a heat exchanger, boiler or other suitable configuration. The purge stream may be heated to a temperature in the range between 50° F. and 450° F., or preferably between 90° F. and 430° F.

The present techniques may also include managing the operating conditions for the test feed stream and other test streams. For example, the feed pressure may be based on the preferred adsorption feed pressure, which may be in the range from 400 pounds per square inch absolute (psia) to 1,400 psia, or in the range from 600 psia to 1,200 psia. Also, the purge pressure may be based on the sales pipeline pressure, which may be in the range from 400 psia to 1400 psia, in the range from 600 psia to 1200 psia. The test system may include compressors, expanders or other pressure adjustment devices to adjust the pressure of the respective streams in the test system.

In certain configurations, the test system may process a test feed stream that predominately comprises hydrocarbons along with one or more contaminants. For example, the test feed stream may be a hydrocarbon containing stream having greater than one volume percent hydrocarbons based on the total volume of the feed stream. Further, the test feed stream may include hydrocarbons and $H_2O$, wherein the $H_2O$ is one of the one or more contaminants and the gaseous feed stream comprises $H_2O$ in the range of 50 parts per million (ppm) molar to 1,500 ppm molar; or in the range of 500 ppm to 1,500 ppm molar. Moreover, the test feed stream may include hydrocarbons and $H_2O$, wherein the $H_2O$ is one of the one or more contaminants and the test feed stream comprises $H_2O$ in the range of two ppm molar to saturation levels in the test feed stream.

In addition, the present techniques may provide a test system that utilizes a rapid cycle swing adsorption process to separate acid gas contaminants from feed streams, such as acid gas from hydrocarbon streams. Acid gas removal technology may be useful for gas reserves exhibit higher concentrations of acid gas (e.g., sour gas resources). Hydrocarbon feed streams vary widely in amount of acid gas, such as from several parts per million acid gas to 90 volume percent (vol. %) acid gas. Non-limiting examples of acid gas concentrations from exemplary gas reserves include concentrations of at least: (a) 1 vol. % $H_2S$, 5 vol. % $CO_2$, (b) 1 vol. % $H_2S$, 15 vol. % $CO_2$, (c) 1 vol. % $H_2S$, 60 vol. % $CO_2$, (d) 15 vol. % $H_2S$, 15 vol. % $CO_2$, and (e) 15 vol. % $H_2S$, 30 vol. % $CO_2$. Accordingly, the present techniques may include equipment to remove various contaminants, such as $H_2S$ and $CO_2$ to desired levels. In particular, the $H_2S$ may be lowered to levels less than 4 ppm, while the $CO_2$ may be lowered to levels less than 1.8 molar percent (%), less than 100 ppm or, preferably, less than 50 ppm. As a further example, the acid gas removal test system may remove $CO_2$ to LNG specifications (e.g., less than or equal to 50 parts per million volume (ppmv) $CO_2$).

In one configuration, the test system may be a test configuration that involves a rapid cycle swing adsorption process, such as a rapid cycle PSA process, to remove test contaminants, such as moisture, from the test feed stream. The specific level of contaminant removal may be related to dew point of desired output product (e.g., the water content should be lower than the water content required to obtain a dew point below the lowest temperature of the stream in subsequent process and is related to the feed pressure). For example, the output stream from the adsorbent bed may be configured to be the cryogenic processing feed stream, which satisfies the cryogenic processing specifications (e.g., approximately −150° F. (−101.1° C.) dew point for NGL processes. The cryogenic processing feed stream specification may include a water content in the stream (e.g., output stream from the adsorbent bed or feed stream to the to be cryogenic processing) to be in the range between 0.0 ppm and 10 ppm, in the range between 0.0 ppm and 5.0 ppm, in the range between 0.0 ppm and 2.0 ppm, or in the range between 0.0 ppm and 1.0 ppm.

In one or more embodiments, the present techniques may be used for any type of swing adsorption process. Non-limiting swing adsorption processes for which the present techniques may include pressure swing adsorption (PSA), vacuum pressure swing adsorption (VPSA), temperature swing adsorption (TSA), partial pressure swing adsorption (PPSA), rapid cycle pressure swing adsorption (RCPSA), rapid cycle thermal swing adsorption (RCTSA), rapid cycle partial pressure swing adsorption (RCPPSA), as well as combinations of these processes, such as pressure and/or temperature swing adsorption. Exemplary kinetic swing adsorption processes are described in U.S. Patent Application Publication Nos. 2008/0282892, 2008/0282887, 2008/0282886, 2008/0282885, 2008/0282884, 2014/0013955, 2017/0056810, 2017/0056813, 2017/0056814 and 2017/0056815, which are each herein incorporated by reference in their entirety. However, rapid cycle swing adsorption processes may be preferred to process the respective feed streams.

In certain configurations, various test streams may be utilized in other steps within the cycle of the swing adsorption process. For example, the product stream may be used as purge source for a subsequent step in the test system. In certain configurations, a dry product stream is conditioned to replicate streams from downstream equipment, such as the residue gas of a demethanizer or fuel gas of an LNG facility, and used as a purge to remove the affluent and blend upstream of the operational system.

Further, in certain configurations of the test system, the present techniques may include a specific process flow to remove contaminants, such as test contaminants (e.g., water ($H_2O$) or acid gas), in the test system. For example, the process may include an adsorbent step and a regeneration step, which form the cycle. The adsorbent step may include passing a test feed stream at a test feed pressure and test feed temperature through an adsorbent bed unit to separate one or more test contaminants from the test feed stream to form a test product stream. The test feed stream may be passed through the adsorbent bed in a forward direction (e.g., from the feed end of the adsorbent bed to the product end of the adsorbent bed). Then, the flow of the test feed stream may be interrupted for a regeneration step. The regeneration step may include one or more depressurization steps, one or more purge steps and/or one or more re-pressurization steps. The depressurization steps may include reducing the pressure of the adsorbent bed unit by a predetermined amount for each successive depressurization step, which may be a single step and/or may be a blowdown step. The depressurization step may be provided in a forward direction or may preferably be provided in a countercurrent direction (e.g., from the product end of the adsorbent bed to the feed end of the adsorbent bed). The purge step may include passing a test purge stream into the adsorbent bed unit, which may be a once through purge step and the test purge stream may be provided in countercurrent flow relative to the test feed stream. The test purge product stream from the purge step may be conducted away and recycled to a specific location in the operational system. Then, the one or more re-pressurization steps may be performed, wherein the pressure within the adsorbent bed unit is increased with each re-pressurization step by a predetermined amount with each successive re-pressurization step. Then, the cycle may be repeated for additional test feed streams and/or the cycle may be adjusted to perform a different cycle for a second test configuration. The cycle duration may be for a period greater than 1 second and less than 1200 seconds, for a period greater than 2 second and less than 600 seconds, for a period greater than 2 second and less than 200 seconds, or for a period greater than 2 second and less than 90 seconds.

Also, the present techniques may be integrated into various configurations, which may include a variety of compositions for the test streams. For example, the same technique may be used to test for removal of test contaminants, such as water, $CO_2$ or $H_2S$. Adsorptive separation processes, apparatus, and systems, as described above, are useful for development and production of hydrocarbons, such as gas and oil processing. Particularly, the provided processes, apparatus, and systems are useful for the rapid, large scale, efficient separation of a variety of target gases from gas mixtures. In addition, the processes, apparatus, and systems may be used to prepare feed products (e.g., natural gas products) by removing contaminants, which may include heavy hydrocarbons (e.g., hydrocarbons having at least two carbon atoms). The provided processes, apparatus, and systems are useful for preparing gaseous feed streams for use in utilities, including separation applications. The separation applications may include dew point control; sweetening and/or detoxification; corrosion protection and/or control; dehydration; heating value; conditioning; and/or purification. Examples of utilities that utilize one or more separation applications include generation of fuel gas; seal gas; non-potable water; blanket gas; instrument and control gas; refrigerant; inert gas; and/or hydrocarbon recovery.

In certain configurations, the present techniques may include a cyclical swing adsorption process for removing contaminants from a feed stream. The process comprising: performing a process to remove one or more contaminants from a feed stream in an operational system; separating one or more streams in the process of the operational system to form a test feed stream; passing the test feed stream to a test system, wherein the test system performs two or more steps in a cycle to perform one or more swing adsorption processes on the test feed stream to remove one or more contaminants from the test feed stream to form a test product stream and a test purge product stream; and mixing at least a portion of the test product stream and the test purge product stream with the streams in the operational system.

In other configurations, various enhancements may be included. For example, the cyclical swing adsorption process may include wherein the one or more swing adsorption processes comprises: a) performing one or more adsorption steps, wherein each of the adsorption steps comprises passing the test feed stream from the operational system through the test swing adsorption system to remove one or more contaminants from the test feed stream and to form a test product stream; b) performing one or more purge steps, wherein each of the purge steps comprise passing a test purge stream through the test swing adsorption system to form a test purge product stream; and c) repeating the steps a) to b) for at least one additional cycle. Further, the cyclical swing adsorption process may include the test purge stream is provided in a counter flow direction relative to the flow of the test feed stream; wherein the one or more contaminants comprise water; wherein the one or more contaminants comprise $CO_2$; wherein the cycle duration is greater than 1 second and less than 600 seconds or is greater than 2 seconds and less than 300 seconds; wherein the feed stream is a hydrocarbon containing stream having greater than one volume percent hydrocarbons based on the total volume of the feed stream; wherein the feed pressure is in the range between 400 pounds per square inch absolute (psia) and 1,400 psia; blending two or more streams from different locations in the process of the operational system to form the test feed stream; wherein each of the two or more streams have different stream compositions; adjusting temperature of the blended stream; increasing pressure of the blended stream prior to passing the test stream to the test system; wherein the operational system is configured to remove one or more contaminants to a pipeline specification, while the test system is configured to remove contaminants to a cryogenic specification; and/or communicating with one or more sensors and/or one or more control valves to manage one of the flow rate, composition, temperature, pressure and any combination thereof within the different streams of the test system. Also, the process may include performing a second swing adsorption process in the test system further comprising: a) performing one or more acid adsorption steps, wherein each of the acid adsorption steps comprises passing a portion of the test product stream from the test swing adsorption system through a second swing adsorption system to remove acid gas from the portion of the test product stream and form a second test product stream; b) performing one or more acid purge steps, wherein each of the acid purge steps comprises passing a portion of the test product stream through the second swing adsorption system to form a second test purge product stream; and c) repeating the steps a) to b) for at least one additional cycle.

In yet another configuration, the present techniques may include a system for testing swing adsorption processes for removing contaminants from a test feed stream. The system include: an operational system configured to perform a process to remove one or more contaminants from a feed stream; a test system in fluid communication with the operational system and comprising: one or more separation units in fluid communication with the operational system and configured to separate one or more streams from the operational system to form a test feed stream; a swing adsorption system comprising one or more adsorbent bed units, wherein each of the one or more adsorbent bed units is configured to separate contaminants from a test feed stream and to output a test product stream in an adsorption step; a recycle unit configured to receive the test product stream and pass at least a portion of the test product stream to one of the one or more adsorbent bed units to perform a purge step and form a test purge product stream; and one or more conduits configured to pass the test product stream and the test purge product stream to operational system.

In other configurations, various enhancements are described. By way of example, the system may further comprise a blending unit in fluid communication with the one or more separation units and configured to blend two or more streams from different locations in the operational system to form the test feed stream; wherein the test system further comprises: a second swing adsorption system comprising one or more second adsorbent bed units, wherein each of the one or more second adsorbent bed units is configured to separate a second contaminant from the at least a portion of the test product stream in an adsorption step, wherein the second contaminant is different from the contaminants; a recycle unit configured to receive the second test product stream and pass at least a portion of the second test product stream to one of the one or more second adsorbent bed units to perform a second purge step and form a second test purge product stream; and one or more conduits configured to pass the second test product stream and the second test purge product stream to operational system; and/or wherein the swing adsorption system is configured to operate on a cycle duration greater than 1 second and less than 600 seconds or greater than 2 seconds and less than 300 seconds. In addition, the system may further comprise a control unit configured to: obtain one of operation conditions or flow rate; calculate the flow rates for the respective streams based on a preferred composition of the blended stream; and calculate any adjustments to pressure and/or temperature in the blended stream; may include one or more sensors configured to measure the operation conditions on the respective streams and to communicate the operation conditions to the control unit; and/or may further comprise one or more flow control mechanisms configured to adjust the flow rate for the respective stream and to communicate the flow rate to the control unit.

In other configurations, a process for removing contaminants from a feed stream and testing one or more swing adsorption processes may be utilized. The process may comprise: performing a process to remove one or more contaminants from a feed stream in an operational system to form a process product stream; separating one or more streams in the process from the operational system to form a test feed stream; passing the test feed stream to a test system, performing one or more swing adsorption processes on the test feed stream in the test system to remove one or more test contaminants from the test feed stream to form a test product stream having less test contaminants than the test feed stream and a test purge product stream containing at least a portion of the one or more test contaminants; mixing at least a portion of the test product stream a first stream in the operational system prior to the forming the process product stream; and mixing at least a portion of the test purge product stream with a second stream in the operational system prior to the forming the process product stream.

In one or more configurations, the process may include that performing one or more swing adsorption processes comprise performing a first swing adsorption process that comprises: a) performing one or more adsorption steps, wherein each of the adsorption steps comprises passing the test feed stream from the operational system through a test swing adsorption system in the test system to remove the one or more test contaminants from the test feed stream and to form the test product stream; b) performing one or more purge steps, wherein each of the purge steps comprise passing a test purge stream through the test swing adsorption system to form the test purge product stream; and c) repeating the steps a) to b) for at least one additional cycle. In addition, the cyclical swing adsorption process may include wherein the test purge stream is provided in a counter flow direction relative to the flow of the test feed stream; and/or wherein the one or more test contaminants comprise water and/or carbon dioxide ($CO_2$).

In other configurations, the process may include various enhancements. For example, the process may comprise performing a second swing adsorption process that comprises: i) performing one or more acid gas adsorption steps, wherein each of the acid gas adsorption steps comprises passing a portion of the test product stream from the test swing adsorption system through a second swing adsorption system to remove acid gas from the portion of the test product stream and form a second test product stream; ii) performing one or more acid gas purge steps, wherein each of the acid gas purge steps comprises passing a portion of the test product stream through the second swing adsorption system to form a second test purge product stream; and iii) repeating the steps i) to ii) for at least one additional cycle. Further, the process may comprise: mixing at least a portion of the second test product stream the first stream or a third stream in the operational system prior to the forming the process product stream, and mixing at least a portion of the second test purge product stream with the second stream or a fourth stream in the operational system prior to the forming the process product stream.

The configurations may include various enhancements. For example, the process may include the swing adsorption processes being performed for a cycle duration greater than 1 second and less than 600 seconds, or a cycle duration greater than 2 seconds and less than 300 seconds; the feed stream may be a hydrocarbon containing stream having greater than one volume percent hydrocarbons based on the total volume of the feed stream; the feed pressure may be in the range between 400 pounds per square inch absolute (psia) and 1,400 psia; blending two or more streams from different locations in the process of the operational system to form the test feed stream, wherein each stream of the two or more streams have a different composition from the remaining streams in the two or more streams; adjusting temperature of the blended stream prior to performing the one or more swing adsorption processes on the test feed stream in the test system; increasing pressure of the blended stream prior to performing the one or more swing adsorption processes on the test feed stream in the test system; wherein the operational system may be configured to remove one or more contaminants to have the process product stream comply with a pipeline specification, while the test system is configured to remove one or more test contaminants to have the test product stream or the second test product stream comply with a cryogenic specification; communicating with one or more sensors and/or one or more control valves to manage one of the flow rate, composition, temperature, pressure and any combination thereof within streams of the test system.

In yet other configurations, a system for testing one or more swing adsorption processes associated with an operational system may be utilized. The system may include: an operational system configured to perform a process to remove one or more contaminants from a feed stream to form a process product stream; a test system in fluid communication with the operational system and comprising: one or more separation units in fluid communication with the operational system and configured to separate one or more streams from the operational system to form a test feed stream; a swing adsorption system comprising one or more adsorbent bed units, wherein each of the one or more adsorbent bed units is configured to receive the test feed stream in an adsorption step and to separate test contaminants from the test feed stream and to output a test product stream having less test contaminants than the test feed stream; a recycle unit in fluid communication with the swing adsorption system and configured to receive the test product stream and to pass at least a portion of the test product stream to one of the one or more adsorbent bed units in a purge step and form a test purge product stream; and one or more conduits configured to pass the test product stream to the operational system and to pass the test purge product stream to the operational system.

In certain configurations, the system may include various enhancements. For example, the system may include a blending unit in fluid communication with the one or more separation units and configured to blend two or more streams from different locations in the operational system to form the test feed stream; a second swing adsorption system comprising one or more second adsorbent bed units, wherein each of the one or more second adsorbent bed units is configured to separate second test contaminants from at least a portion of the test product stream in an adsorption step, wherein the second test contaminants is different from the test contaminants, a recycle unit configured to receive the second test product stream and pass at least a portion of the second test product stream to one of the one or more second adsorbent bed units to perform a second purge step and form a second test purge product stream, and one or more conduits configured to pass the second test product stream to the operational system and to pass the second test purge product stream to the operational system; a control unit configured to: obtain measured data from a plurality of locations in the operational system, wherein the measured data includes one or more of operation conditions, flow rates and any combination thereof, calculate a flow rate for each of the plurality of locations in the operational system, wherein the flow rate for each of the plurality of locations is based on a predetermined test composition of the blended stream, and calculate an adjustment to an operation condition in the blended stream, wherein the operation condition comprise one of pressure, temperature and any combination thereof; one or more sensors configured to monitor each of the plurality of locations to obtain the measurement data and to communicate the measurement data to the control unit; and/or one or more flow control mechanisms configured to adjust the flow rate for the each of the plurality of locations and to communicate the flow rate for each of the plurality of locations to the control unit. The present techniques may be further understood with reference to the FIGS. 1 to 3 below.

FIG. 1 is a three-dimensional diagram of the swing adsorption system 100 having six adsorbent bed units and interconnecting piping. While this configuration is a specific example, the present techniques broadly relate to adsorbent bed units that can be deployed in a symmetrical orientation, or non-symmetrical orientation and/or combination of a plurality of hardware skids. Further, this specific configuration is for exemplary purposes as other configurations may include different numbers of adsorbent bed units.

In this system, the adsorbent bed units, such as adsorbent bed unit 102, may be configured for a cyclical swing adsorption process for removing contaminants from feed streams (e.g., fluids, gaseous or liquids). For example, the adsorbent bed unit 102 may include various conduits (e.g., conduit 104) for managing the flow of fluids through, to or from the adsorbent bed within the adsorbent bed unit 102. These conduits from the adsorbent bed units 102 may be coupled to a manifold (e.g., manifold 106) to distribute the flow of the stream to, from or between components. The adsorbent bed within an adsorbent bed unit may separate one or more contaminants from the feed stream to form a product stream. As may be appreciated, the adsorbent bed units may include other conduits to control other fluid steams as part of the process, such as purge streams, depressurizations streams, and the like. Further, the adsorbent bed unit may also include one or more equalization vessels, such as equalization vessel 108, which are dedicated to the adsorbent bed unit and may be dedicated to one or more step in the swing adsorption process.

As an example, which is discussed further below in FIG. 2, one or more of the adsorbent bed units, may be utilized in a configuration that is integrated with an operational system to provide different compositions of streams for measuring and verifying operation of a test system in a specific configuration. As noted above, a test system may be integrated with various valves, manifolds and conduits to provide fluid flow paths for different test streams to measure the operation of a test system. In contrast to conventional systems, which is an isolated configuration from operational systems, the present techniques provide a system that utilizes streams from an operational system. A schematic diagram 200 of an exemplary test system 202 integrated with an operational system 204 is shown below in FIG. 2.

Figure 2:
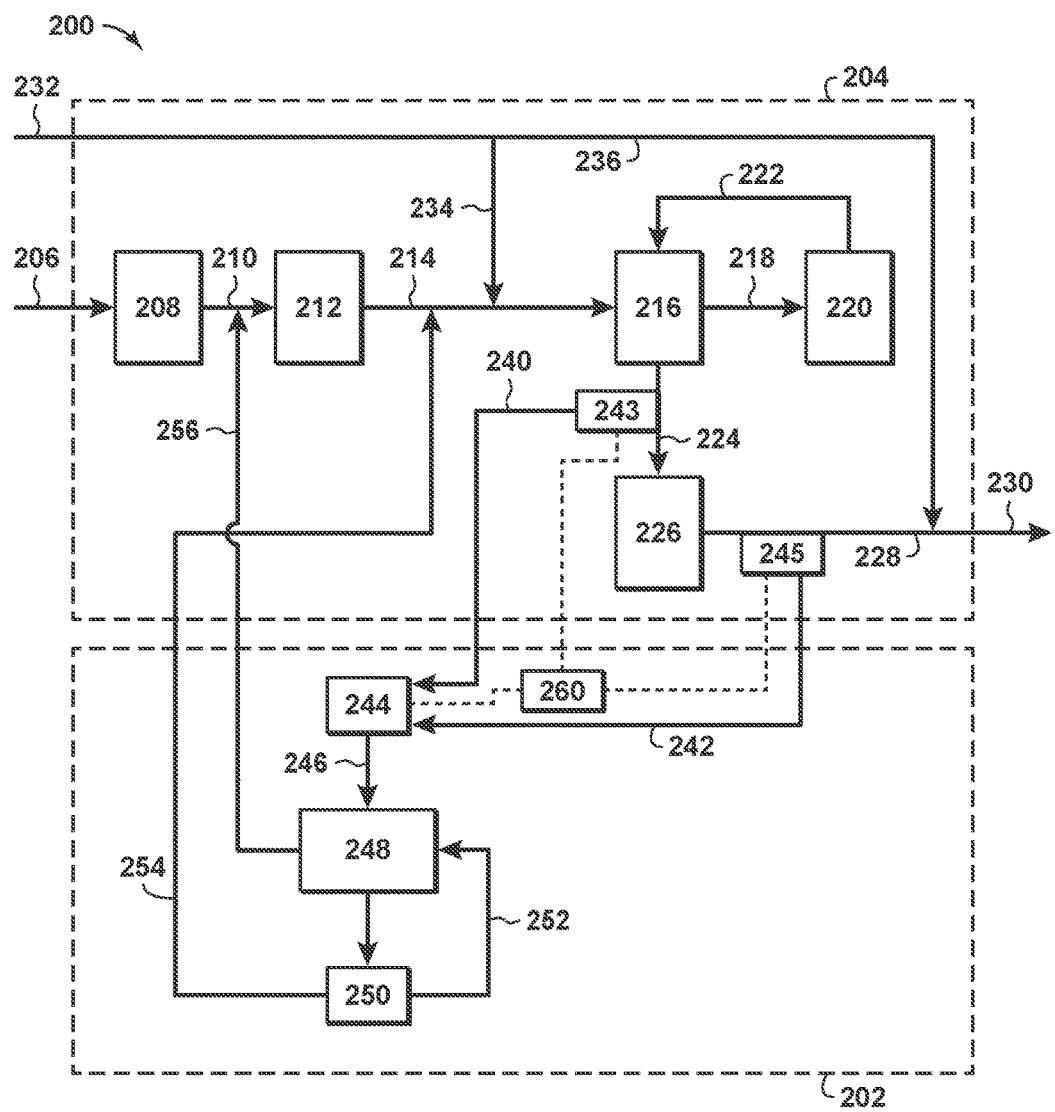
FIG. 2 is a diagram of an exemplary test system for removing contaminants from a test feed stream integrated with an operational system in accordance with an embodiment of the present techniques.

FIG. 2 is a diagram 200 of an exemplary test system 202 for removing contaminants from a test feed stream integrated with an operational system 204. In this diagram 200, a test system 202 is utilized to test the performance of a swing adsorption processes and technology within an operational system 204, which may be an existing facility, without upsetting the performance of the operational system 204. To test the performance of the swing adsorption technology at multiple operating points, the configuration involves conduits that provide several fluid connection pathways, such as conduits 240, 242, 254 and 256, to the streams within the operational system 204 at different locations or different stages of gas purification. The conduits provide a mechanism to create a blended composition for a desired test condition in the test blending unit 244, which is then passed to the test swing adsorption system 248, as the test feed stream. In this configuration, two streams from different source locations are blended to provide a stream that contains the desired amount of water ($H_2O$). Then, the test feed stream is processed by the test swing adsorption system 248 and the resulting test product stream and/or waste gas stream are mixed with the operational system via conduits 254 and 256. Thus, the test streams are provided to the operational system 204 in a manner to maintain stable concentration and flowrate. In this configuration, the purge stream containing the affluent and the product stream that is devoid of moisture is returned back to the front end of the operational system 204 following the inlet separation unit 208. Returning the streams from the test swing adsorption system 248 upstream of the removal locations maintains the stream in the operational system 204, such that is does not result in off-specification product even if the test swing adsorption system 248 does not operate as predicted. As a recycle is provided within the operational system 204, the gas flowrate and composition may be stable as long as the feed rate to the test swing adsorption system 248 is stable.

The operational system 204 may include various units, such as units 208, 212, 216, 220 and 226, that are configured to process the inlet stream to provide a sales stream (e.g., a sales gas stream). The inlet separation unit 208 is configured to receive the inlet stream 206 and to separate one or more contaminants from the remaining stream, which is passed via conduit 210 to the compressor 212. The composition of the inlet stream temperature may be in a range between 50°

F. and 120° F. The compression unit 212 is configured to compress and cool the stream from conduit 210 from a first pressure to a second pressure, which is higher than the first pressure. The compressed stream is passed via conduit 214 to the gas to gas exchanger unit 216. The gas to gas exchanger unit 216 is configured to increase the temperature of the compressed stream through heat exchange with the hydrocarbon rich stream in conduit 222 from the amine unit 220, which has its temperature decreased in the gas to gas exchanger unit 216. From the gas to gas exchanger unit 216, the stream is passed via conduit 218 to the amine unit 220. The amine unit 220 is configured to remove a portion of the acid gas (e.g., $CO_2$ and $H_2S$) from the stream. The acid gas is conducted away from the operational system (not shown), while the hydrocarbon rich stream is passed via conduit 222 to the gas to gas exchanger unit 216 and then via conduit 224 to the TEG unit 226. The TEG unit 226 is configured to remove water ($H_2O$) from the stream. While a portion of the water is removed from the operational system 204 (not shown), the remaining stream is passed to sales gas via conduit 228 and 230. The contaminants in the configurations may be removed during a regeneration step (not shown). For example, contaminants, such as $CO_2$ and $H_2S$, may be removed during the amine regeneration step and $H_2O$ may be removed in the TEG regeneration step.

In addition, the operational system 204 may include a bypass configuration, as well. The bypass configuration may include a high pressure inlet conduit 232, which passes a high pressure inlet stream to the conduits 234 and 236. The conduit 234 is configured to pass a portion of the high pressure inlet stream to conduit 214, while conduit 236 is configured to pass the remaining portion of the high pressure inlet stream to conduits 228 and 230.

The test system 202 may include various units, such as units 243, 244, 245, 248 and 250, which are configured to process a test stream for the specific test configuration. In this configuration, the test swing adsorption system 248 may include one or more adsorbent bed units that are configured to operate a test cycle, which may each be performing different steps in the cycle, which may be remove test contaminants. By way of example, this configuration may include an adsorption step and a regeneration step (e.g., a purge step). For the adsorption step, the test blending unit 244 is configured to manage the composition of the test feed stream by mixing the stream in conduit 240 with the stream in conduit 242. The stream in conduit 240 may be provided by the separation unit 243, which may be configured to provide a portion of the stream in conduit 224 to the test system 202 and pass the remaining portion through the conduit 224. Similarly, the stream in conduit 242 may be provided by the separation unit 245, which may be configured to provide a portion of the stream in conduit 228 to the test system 202 and pass the remaining portion through the conduit 228. The separation units 243 and 245 may be a flow diverter, valve, separator, conduit or other suitable device to divert a portion of the stream from the conduit or flow path. The stream in conduit 240 has a higher concentration of $H_2O$ as compared to the stream in conduit 242, which has had a portion of the $H_2O$ removed via the TEG unit 226. The blended stream is provided to the test swing adsorption system 248 as the test feed stream via conduit 246. The test swing adsorption system 248 removes $H_2O$ from the test feed stream and passes a test product stream from the test swing adsorption system 248 to a recycle unit 250. For the regeneration step, the recycle unit 250 passes a portion of the test product stream to the test swing adsorption system 248 as a test purge stream via conduit 252, while the remaining portion of the test product stream is passed via conduit 254 to be mixed with the stream in conduit 214. The test purge stream is passed to the test swing adsorption system 248 and interacts with the $H_2O$ to remove the $H_2O$ from the adsorbent bed unit in the test swing adsorption system 248. The resulting test purge product steam is passed via conduit 256 to the conduit 210 in the operational system 204.

To manage and monitor the test system 202, a control system may be utilized to manage the flow of fluids and obtain measurements from the different streams. By way of example, the control system may include various sensors and control valves may be utilized with a control unit. The control unit may be configured to communicate with a first flow rate meter that is configured to measure the flow rate through the conduit 240 and communicate the first measured flow rate to the control unit, and with a first flow valve that is configured to adjust the amount of flow through the conduit 240 into the test blending unit 244. Similarly, the control unit may be configured to communicate with a second flow rate meter that is configured to measure the flow rate through the conduit 242 and communicate the second measured flow rate to the control unit, and with a second flow valve that is configured to adjust the amount of flow through the conduit 242 into the test blending unit 244. In this configuration, the control unit may control the blending of the different streams to provide a desired composition for the test feed stream. The control unit may be configured to provide a desired flow rate and moisture content in conduit 246. Furthermore, in other configurations, the control unit can be used to adjust the pressure and temperature of the flow in conduit 246 to the desired range, which may involve additional hardware such as heat exchanger and valves.

By way of example, a control unit 260 may be configured to communicate with sensors and flow control mechanisms associated with the test blending unit 244, the first separation unit 243 and the second separation unit 245, which is shown by the dotted lines. In this configuration, the sensors may be configured to measure the operation conditions, such as pressure, temperature, flow rate and/or composition, on the respective streams and to communicate the operation conditions to the control unit 260. The flow control mechanisms may be configured to adjust the flow rate for the respective stream and to communicate the flow rate to the control unit 260. The control unit 260 may be configured to obtain the operation conditions and/or flow rate; to calculate the flow rates for the respective streams based on a preferred composition of the blended stream, and/or to calculate any adjustments to pressure and/or temperature in the blended stream.

Figure 3:
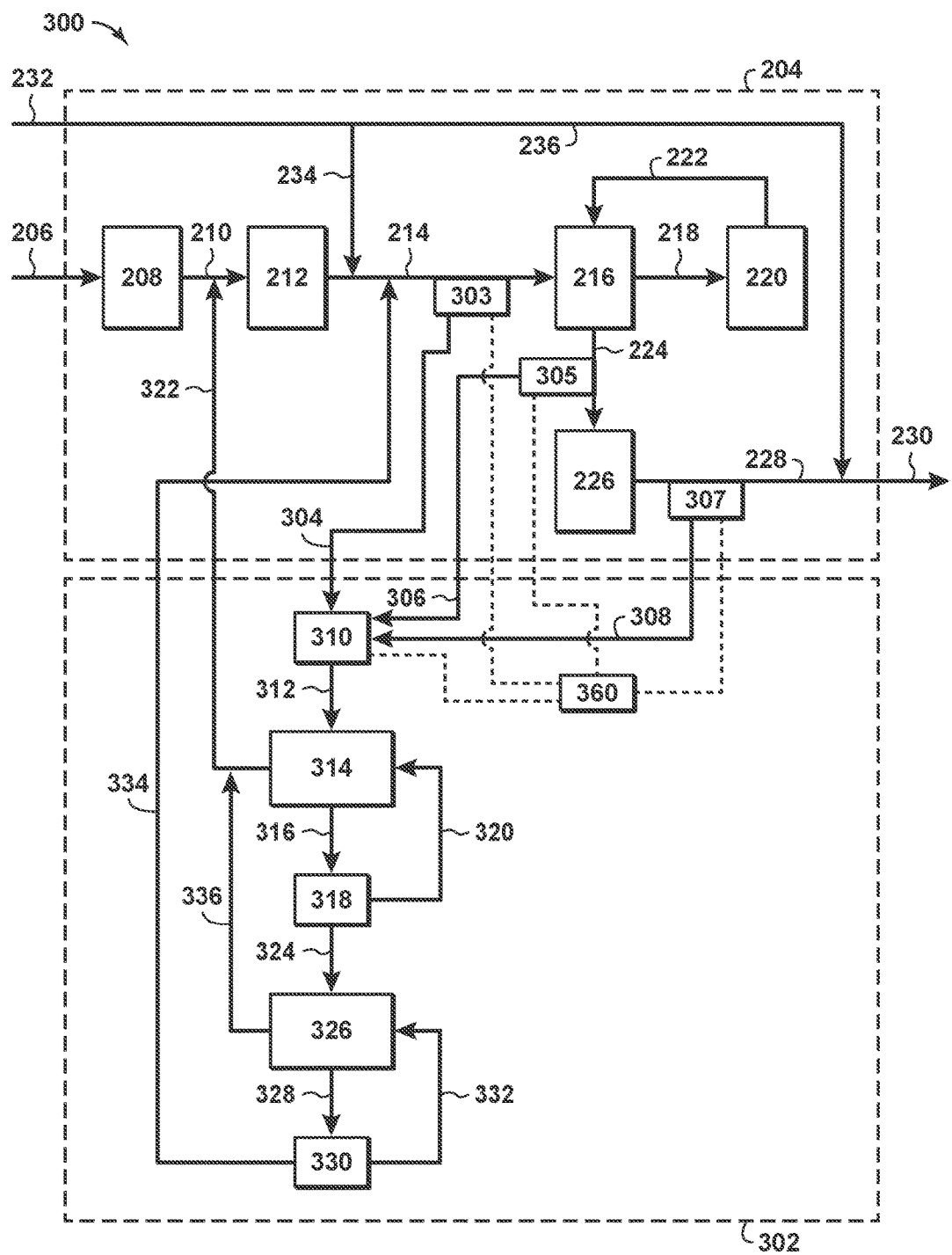
FIG. 3 is a diagram of another exemplary test system for removing contaminants from a test feed stream integrated with an operational system in accordance with an embodiment of the present techniques.

Another configuration is shown in FIG. 3. FIG. 3 is a diagram 300 of an exemplary test system 302 for removing contaminants from a test feed stream integrated with an operational system 204 in accordance with an embodiment of the present techniques. In this diagram 300, the operational system 204 utilizes the units and conduits with the same reference characters, as described above in the operational system 204 of FIG. 2. However, in this diagram 300, a test system 302 is utilized to test the performance of two swing adsorption systems 314 and 326 (e.g., swing adsorption processes) with the operational system 204. To test the performance of these different swing adsorption processes at multiple operating points, this configuration involves valves and conduits that provide several fluid connection pathways, such as conduits 304, 306, 308, 322 and 334, to the streams within the operational system 204 at different stages of gas purification.

The test system 302 may include various units, such as units 303, 305, 307, 310, 314, 318, 326 and 330, which are configured to process a blended stream for a specific test configuration. In this configuration, two test swing adsorption systems 314 and 326 may each include one or more adsorbent bed units that are configured to operate a test cycle, which may each be performing different steps in the respective cycle. By way of example, each of these test swing adsorption systems 314 and 326 may perform an adsorption step and a regeneration step (e.g., a purge step). In the first test swing adsorption system 314, the adsorption step involves blending various streams in the test blending unit 310. The stream in conduit 304 may be provided by the separation unit 303, which may be configured to provide a portion of the stream in conduit 214 to the test system 302 and pass the remaining portion through the conduit 214. Similarly, the stream in conduit 306 may be provided by the separation unit 305, which may be configured to provide a portion of the stream in conduit 224 to the test system 302 and pass the remaining portion through the conduit 224. Further, the stream in conduit 308 may be provided by the separation unit 307, which may be configured to provide a portion of the stream in conduit 228 to the test system 302 and pass the remaining portion through the conduit 228. The separation units 303, 305 and 307 may be a flow diverter, valve, separator, conduit or other suitable device to divert a portion of the stream from the respective conduit or flow path. The test blending unit 310 is configured to manage the composition of the test feed stream by mixing the stream in conduit 304 with the stream in conduit 306 and with the stream in conduit 308. The stream in conduit 304 has a higher concentration of $CO_2$ as compared to the streams in conduits 306 and 308, the stream in conduit 306 has a higher concentration of $H_2O$ as compared to the stream in conduit 308, which has had a portion of the $H_2O$ removed via the TEG unit 226. The blended stream is provided to the first test swing adsorption system 314 as the first test feed stream via conduit 312. The first test swing adsorption system 314 is configured to remove $H_2O$ from the first test feed stream and passes a first test product stream from the first test swing adsorption system 314 to a first recycle unit 318 via conduit 316. For the regeneration step in the first test swing adsorption system 314, the first recycle unit 318 passes a portion of the first test product stream to the first test swing adsorption system 314 as a first test purge stream via conduit 320, while the remaining portion of the first test product stream is passed via conduit 324 to the second test swing adsorption systems 326. The first test purge stream is passed to the first test swing adsorption system 314 and interacts with the $H_2O$ to remove the $H_2O$ from the adsorbent bed unit in the first test swing adsorption system 314. The resulting first test purge product steam is passed via conduit 322 to the conduit 210 in the operational system 204.

Similarly, the second test swing adsorption system 326 in this configuration performs an adsorption step and a regeneration step. In the adsorption step, the remaining portion of the first test product stream is passed via conduit 324 to the second test swing adsorption systems 326 as the second test feed stream. The second test swing adsorption system 326 is configured to remove $CO_2$ and $H_2S$ from the second test feed stream and passes a second test product stream from the second test swing adsorption system 326 to a second recycle unit 330 via conduit 328. From the second recycle unit 330, a portion of the second test product stream is passed via conduit 332 to the second test swing adsorption system 326 as the second purge stream, while the remaining portion of the second test product stream is passed via conduit 334 to be mixed with the stream in conduit 214. For the regeneration step in the second test swing adsorption system 326, the second test purge stream is passed to the second test swing adsorption system 326 and interacts with the $CO_2$ and $H_2S$ to remove the $CO_2$ and $H_2S$ from the adsorbent bed unit in the second test swing adsorption system 326. The resulting second test purge product steam is passed via conduit 336 to be mixed with the stream in conduit 322 and then conduit 210 in the operational system 204.

Beneficially, three stream from different source locations are blended to provide a stream that contains the desired amount of water ($H_2O$) and $CO_2$. By passing the test streams to specified locations within the operational system, the operational system may maintain stable concentration and flowrates. Further, the returning of the streams at the specific locations maintains the production of streams of the operational system, such that the produced stream does not exceed the desired specifications even if the test swing adsorption systems 314 and 326 do not operate as predicted.

Further, the configuration may also be adjusted for other enhancements. For example, the configuration may be adjusted based on the state of the test streams that are conducted away from the test system (e.g., pressure, temperature, and/or composition). The return points may be selected to utilize the spare capacity of existing equipment. Accordingly, the test product and/or waste streams may be compressed or depressurized to a desired pressure or existing compression can be used for the duration of test phase. Additional instrumentation may also be use that may exceed the requirements for a specific application to understand the performance of the test system with the blended gas composition.

Beneficially, this configuration may be utilized with different volumes and flow rates that are more realistic to commercial applications (e.g., operational conditions).

Similar to the control system described in relation to FIG. 2, a control system may be utilized to manage the flow of fluids and obtain measurements from the different streams in the test system 302. By way of example, the control system may include various sensors and control valves may be utilized with a control unit. The control unit may be configured to communicate with a first flow rate meter that is configured to measure the flow rate through the conduit 240 and communicate the first measured flow rate to the control unit, and with a first flow valve that is configured to adjust the amount of flow through the conduit 240 into the test blending unit 244. Similarly, the control unit may be configured to communicate with a second flow rate meter that is configured to measure the flow rate through the conduit 242 and communicate the second measured flow rate to the control unit, and with a second flow valve that is configured to adjust the amount of flow through the conduit 242 into the test blending unit 244. In this configuration, the control unit may control the blending of the different streams to provide a desired composition for the test feed stream.

By way of example, a control unit 360 may be configured to communicate with sensors and flow control mechanisms associated with the test blending unit 310 the first separation unit 303, the second separation unit 305, and the third separation unit 307, which is shown via dotted lines. In this configuration, the sensors may be configured to measure the operation conditions, such as pressure, temperature, flow rate and/or composition, on the respective streams and to communicate the operation conditions to the control unit 360. The flow control mechanisms may be configured to adjust the flow rate for the respective stream and to communicate the flow rate to the control unit 360. The control unit 360 may be configured to obtain the operation conditions and/or flow rate; to calculate the flow rates for the respective streams based on a preferred composition of the blended stream, and/or to calculate any adjustments to pressure and/or temperature in the blended stream.

As may be appreciated, the use of the test product stream as source for the test purge stream is utilized to replicate other streams that may be provided from a downstream source. The test purge stream may represent a residue gas of a demethanizer or a fuel gas of an LNG facility. Accordingly, different variations in the pressure, temperature and composition may be utilized to replicate these streams and used as a purge stream to remove the affluent and blend upstream of the main processing facility. These variations may be achieved through the use of various devices, such as heat exchangers, compressors, expanders, valves, and other equipment.

In one or more embodiments, the adsorbent bed unit in the test system may include an adsorbent bed that can be used for the separation of a target gas form a gaseous mixture. The adsorbent is usually comprised of an adsorbent material supported on a non-adsorbent support, or contactor. Such contactors contain substantially parallel flow channels wherein 20 volume percent, preferably 15 volume percent or less of the open pore volume of the contactor, excluding the flow channels, is in pores greater than about 20 angstroms. A flow channel is taken to be that portion of the contactor in which gas flows, if a steady state pressure difference is applied between the points or places at which a feed stream enters the contactor and the point or place at which a product stream leaves the contactor. In the contactor, the adsorbent is incorporated into the wall of the flow channel.

In certain configurations, the material in the adsorbent bed unit may include an adsorbent material supported on a non-adsorbent support. Non-limiting examples of adsorbent materials may include alumina, microporous zeolites, carbons, cationic zeolites, high silica zeolites, highly siliceous ordered mesoporous materials, sol gel materials, aluminum phosphorous and oxygen (ALPO) materials (microporous and mesoporous materials containing predominantly aluminum phosphorous and oxygen), silicon aluminum phosphorous and oxygen (SAPO) materials (microporous and mesoporous materials containing predominantly silicon aluminum phosphorous and oxygen), metal organic framework (MOF) materials (microporous and mesoporous materials comprised of a metal organic framework) and zeolitic imidazolate frameworks (ZIF) materials (microporous and mesoporous materials comprised of zeolitic imidazolate frameworks). Other materials include microporous and mesoporous sorbents functionalized with functional groups. Examples of functional groups, which may be used for $CO_2$ removal, may include primary, secondary, tertiary amines and other non protogenic basic groups such as amidines, guanidines and biguanides.

As an example, the adsorbent bed unit in the well system may include a housing, which may include a head portion and other body portions, that forms a substantially gas impermeable partition, an adsorbent bed disposed within the housing and a plurality of valves (e.g., poppet valves) providing fluid flow passages through openings in the housing between the interior region of the housing and locations external to the interior region of the housing. Each of the poppet valves may include a disk element that is seatable within the head or a disk element that is seatable within a separate valve seat inserted within the head (not shown). The configuration of the poppet valves may be any variety of valve patterns or configuration of types of poppet valves. As an example, the adsorbent bed unit may include one or more poppet valves, each in flow communication with a different conduit associated with different streams. The poppet valves may provide fluid communication between the adsorbent bed and one of the respective conduits, manifolds or headers. The term "in direct flow communication" or "in direct fluid communication" means in direct flow communication without intervening valves or other closure means for obstructing flow. As may be appreciated, other variations may also be envisioned within the scope of the present techniques.

The adsorbent bed comprises a solid adsorbent material capable of adsorbing one or more components from the feed stream. Such solid adsorbent materials are selected to be durable against the physical and chemical conditions within the adsorbent bed unit and can include metallic, ceramic, or other materials, depending on the adsorption process.

To provide fluid flow paths through the adsorbent bed unit, the valve assemblies may include poppet valves, which each may include a disk element connected to a stem element which can be positioned within a bushing or valve guide. The stem element may be connected to an actuating means, such as actuating means (not shown), which is configured to have the respective valve impart linear motion to the respective stem. As may be appreciated, the actuating means may be operated independently for different steps in the process to activate a single valve or a single actuating means may be utilized to control two or more valves. Further, while the openings may be substantially similar in size, the openings and inlet valves for inlet manifolds may have a smaller diameter than those for outlet manifolds, given that the gas volumes passing through the inlets may tend to be lower than product volumes passing through the outlets. Further, while this configuration has valve assemblies, the number and operation of the valves may vary (e.g., the number of valves) based on the specific cycle being performed.

In one or more embodiments, the rapid cycle swing adsorption process in the present techniques is a rapid cycle temperature swing adsorption (RCTSA) and a pressure swing adsorption (RCPSA). For example, the total cycle times are typically less than 1200 seconds, less than 600 seconds, preferably less than 200 seconds, more preferably less than 90 seconds, and even more preferably less than 60 seconds.

In view of the many possible embodiments to which the principles of the disclosed invention may be applied, it should be recognized that the illustrative embodiments are only preferred examples of the invention and should not be taken as limiting the scope of the invention.

What is claimed is:

1. A process for removing contaminants from a feed stream and testing one or more swing adsorption processes, the process comprising:
   performing a process to remove one or more contaminants from a feed stream in an operational system to form a process product stream;
   separating one or more streams in the process from the operational system to form a test feed stream;
   passing the test feed stream to a test system;
   performing one or more swing adsorption processes on the test feed stream in the test system to remove one or more test contaminants from the test feed stream to form a test product stream having less test contaminants than the test feed stream and a test purge product stream containing at least a portion of the one or more test contaminants;

mixing at least a portion of the test product stream with a first stream in the operational system prior to the forming the process product stream; and mixing at least a portion of the test purge product stream with a second stream in the operational system prior to the forming the process product stream.

2. The process of claim 1, wherein the performing one or more swing adsorption processes comprise performing a first swing adsorption process that comprises:

a) performing one or more adsorption steps, wherein each of the adsorption steps comprises passing the test feed stream from the operational system through a test swing adsorption system in the test system to remove the one or more test contaminants from the test feed stream and to form the test product stream;

b) performing one or more purge steps, wherein each of the purge steps comprise passing a test purge stream through the test swing adsorption system to form the test purge product stream; and c) repeating the steps a) to b) for at least one additional cycle.

3. The process of claim 2, wherein the test purge stream is provided in a counter flow direction relative to the flow of the test feed stream.

4. The process of claim 2, wherein the one or more test contaminants comprise water.

5. The process of claim 2, wherein the one or more test contaminants comprise carbon dioxide ($CO_2$).

6. The process of claim 2, wherein the performing the one or more swing adsorption processes comprises performing a second swing adsorption process that comprises:

i) performing one or more acid gas adsorption steps, wherein each of the acid gas adsorption steps comprises passing a portion of the test product stream from the test swing adsorption system through a second swing adsorption system to remove acid gas from the portion of the test product stream and form a second test product stream;

ii) performing one or more acid gas purge steps, wherein each of the acid gas purge steps comprises passing a portion of the test product stream through the second swing adsorption system to form a second test purge product stream; and iii) repeating the steps i) to ii) for at least one additional cycle.

7. The process of claim 6, further comprising:
mixing at least a portion of the second test product stream the first stream or a third stream in the operational system prior to the forming the process product stream; and mixing at least a portion of the second test purge product stream with the second stream or a fourth stream in the operational system prior to the forming the process product stream.

8. The process of claim 1, wherein the one or more swing adsorption processes are performed for a cycle duration greater than 1 second and less than 600 seconds.

9. The process of claim 1, wherein the one or more swing adsorption processes are performed for a cycle duration greater than 2 seconds and less than 300 seconds.

10. The process of claim 1, wherein the feed stream is a hydrocarbon containing stream having greater than one volume percent hydrocarbons based on the total volume of the feed stream.

11. The process of claim 1, wherein the feed pressure is in the range between 400 pounds per square inch absolute (psia) and 1,400 psia.

12. The process of claim 1, further comprising blending two or more streams from different locations in the process of the operational system to form the test feed stream, wherein each stream of the two or more streams have a different composition from the remaining streams in the two or more streams.

13. The process of claim 12, further comprising adjusting temperature of the test feed stream prior to performing the one or more swing adsorption processes on the test feed stream in the test system.

14. The process of claim 12, further comprising increasing pressure of the test feed stream prior to performing the one or more swing adsorption processes on the test feed stream in the test system.

15. The process of claim 1, wherein the operational system is configured to remove one or more contaminants to have the process product stream comply with a pipeline specification, while the test system is configured to remove one or more test contaminants to have the test product stream or the second test product stream comply with a cryogenic specification.

16. The process of claim 1, further comprising communicating with one or more sensors and/or one or more control valves to manage one of the flow rate, composition, temperature, pressure and any combination thereof within streams of the test system.

17. A system for testing one or more swing adsorption processes associated with an operational system, the system comprising:

an operational system configured to perform a process to remove one or more contaminants from a feed stream to form a process product stream;

a test system in fluid communication with the operational system and comprising:

one or more separation units in fluid communication with the operational system and configured to separate one or more streams from the operational system to form a test feed stream;

a swing adsorption system comprising one or more adsorbent bed units, wherein each of the one or more adsorbent bed units is configured to receive the test feed stream in an adsorption step and to separate test contaminants from the test feed stream and to output a test product stream having less test contaminants than the test feed stream;

a recycle unit in fluid communication with the swing adsorption system and configured to receive the test product stream and to pass at least a portion of the test product stream to one of the one or more adsorbent bed units in a purge step and form a test purge product stream; and one or more conduits configured to pass the test product stream to the operational system and to pass the test purge product stream to the operational system.

18. The system of claim 17, further comprising a blending unit in fluid communication with the one or more separation units and configured to blend two or more streams from different locations in the operational system to form the test feed stream.

19. The system of claim 17, wherein the test system further comprises:

a second swing adsorption system comprising one or more second adsorbent bed units, wherein each of the one or more second adsorbent bed units is configured to separate second test contaminants from at least a portion of the test product stream in an adsorption step, wherein the second test contaminants is different from the test contaminants;
a recycle unit configured to receive the second test product stream and pass at least a portion of the second test product stream to one of the one or more second adsorbent bed units to perform a second purge step and form a second test purge product stream; and
one or more conduits configured to pass the second test product stream to the operational system and to pass the second test purge product stream to the operational system.

20. The system of claim 18, further comprising a control unit configured to:
obtain measured data from a plurality of locations in the operational system, wherein the measured data includes one or more of operation conditions, flow rates and any combination thereof;
calculate a flow rate for each of the plurality of locations in the operational system, wherein the flow rate for each of the plurality of locations is based on a predetermined test composition of the test feed stream; and
calculate an adjustment to an operation condition in the test feed stream, wherein the operation condition comprise one of pressure, temperature and any combination thereof.

21. The system of claim 20, further comprising one or more sensors configured to monitor each of the plurality of locations to obtain the measurement data and to communicate the measurement data to the control unit.

22. The system of claim 21, further comprising one or more flow control mechanisms configured to adjust the flow rate for the each of the plurality of locations and to communicate the flow rate for each of the plurality of locations to the control unit.

23. The system of claim 17, wherein the swing adsorption system is configured to operate on a cycle duration greater than 1 second and less than 600 seconds.

24. The system of claim 17, wherein the swing adsorption system is configured to operate on a cycle duration greater than 2 seconds and less than 300 seconds.

* * * * *